United States Patent
Agnihotra et al.

(10) Patent No.: US 11,940,403 B2
(45) Date of Patent: Mar. 26, 2024

(54) FOOD ALLERGEN DETECTION DEVICE AND METHODS OF USE THEREOF

(71) Applicant: Amulet, Inc., Madison, WI (US)

(72) Inventors: Srikanth Rao Agnihotra, Tyngsboro, MA (US); Madanodaya Sundhoro, Lowell, MA (US); Brent Amberger, Dracut, MA (US); Abigail Barnes, Madison, WI (US); Joseph Belbruno, Hanover, NH (US); Seung Hyuk Noh, Providence, RI (US); Jeanette Numbers, Providence, RI (US); Elizabeth Soucy, Seattle, WA (US)

(73) Assignee: Amulet, Inc., Madison, WI (US)

( * ) Notice: Subject to any disclaimer, the term of this patent is extended or adjusted under 35 U.S.C. 154(b) by 1178 days.

(21) Appl. No.: 16/609,943

(22) PCT Filed: May 1, 2018

(86) PCT No.: PCT/US2018/030494
§ 371 (c)(1),
(2) Date: Oct. 31, 2019

(87) PCT Pub. No.: WO2018/204390
PCT Pub. Date: Nov. 8, 2018

(65) Prior Publication Data
US 2020/0200694 A1 Jun. 25, 2020

Related U.S. Application Data

(60) Provisional application No. 62/500,412, filed on May 2, 2017.

(51) Int. Cl.
*G01N 27/12* (2006.01)
*G01N 27/04* (2006.01)
(Continued)

(52) U.S. Cl.
CPC ......... *G01N 27/126* (2013.01); *G01N 27/045* (2013.01); *C08K 3/041* (2017.05);
(Continued)

(58) Field of Classification Search
CPC .... G01N 27/126; G01N 27/045; G01N 33/02; G01N 33/68; G01N 2600/00;
(Continued)

(56) References Cited

U.S. PATENT DOCUMENTS

| | | |
|---|---|---|
| 6,461,873 B1 | 10/2002 | Catania et al. |
| 2005/0054078 A1 | 3/2005 | Miller et al. |

(Continued)

FOREIGN PATENT DOCUMENTS

| | | |
|---|---|---|
| WO | WO-2012/034115 A1 | 3/2012 |
| WO | WO-2015/017442 A2 | 2/2015 |

OTHER PUBLICATIONS

Acunha et al., "Recent advances in the application of capillary electromigration methods for food analysis and Foodomics," Electrophoresis, vol. 37, pp. 111-141. (2016).
(Continued)

*Primary Examiner* — Jill A Warden
*Assistant Examiner* — John McGuirk
(74) *Attorney, Agent, or Firm* — Karen A. LeCuyer; DeWitt LLP

(57) ABSTRACT

A device for the detection of a food allergen includes a sensor having a printed circuit board and a chip comprising a molecularly imprinted polymer (MIP) and a non-imprinted polymer (NIP); a reservoir comprising a liquid; and a chamber for mixing the liquid with a food.

18 Claims, 22 Drawing Sheets

(51) Int. Cl.
  *G01N 33/02* (2006.01)
  *G01N 33/68* (2006.01)
  *C08K 3/04* (2006.01)

(52) U.S. Cl.
  CPC ........ *C08K 2201/001* (2013.01); *G01N 33/02* (2013.01); *G01N 33/68* (2013.01); *G01N 2600/00* (2013.01)

(58) Field of Classification Search
  CPC ... C08L 29/04; C08K 3/041; C08K 2201/001; Y02P 20/582
  See application file for complete search history.

(56) References Cited

U.S. PATENT DOCUMENTS

| | | | | |
|---|---|---|---|---|
| 2007/0243625 | A1* | 10/2007 | Oguri | G01N 33/74 436/164 |
| 2008/0305211 | A1* | 12/2008 | Ahmedna | C12Y 304/23001 426/63 |
| 2012/0264232 | A1* | 10/2012 | Kramer | G01N 33/02 422/69 |
| 2016/0209420 | A1 | 7/2016 | Barnes et al. | |

OTHER PUBLICATIONS

Bongaers, et al. "A MIP-based biomimetic sensor for the impedimetric detection of histamine in different pH environments," Phys. Status Solidi A., vol. 207, No. 4, pp. 837-843. (2010).

International Search Report and Written Opinion in International Application No. PCT/US2018/030494, dated Jul. 16, 2018.

Schirhagl et al., "Immunosensing with artificial antibodies in organic solvents or complex matrices," Sensors and Actuators B: Chemical, vol. 173, pp. 585-590. (2012).

Wackers et al., "Array Formatting of the Heat-Transfer Method {HTM) for the Detection of Small Organic Molecules by Molecularly Imprinted Polymers," Sensors, vol. 14. No. 6. pp. 11016-11030. (2014).

* cited by examiner

FOOD ALLERGEN DETECTION DEVICE AND METHODS OF USE THEREOF

CROSS-REFERENCE TO RELATED PATENT APPLICATIONS

This application is a U.S. National Phase Application under 35 U.S.C. § 371 of International Application No. PCT/US2018/030494, filed on May 1, 2018, which claims the benefit of priority to U.S. Provisional Application No. 62/500,412, filed on May 2, 2017, and which are each incorporated herein by reference in their entireties for all purposes.

BACKGROUND

Many people suffer from allergies to foods of various types. While the severity of allergic reactions varies, many reactions can be fatal. Preventing the inadvertent ingestion of and/or exposure to food allergens is a concern for many. Present allergen-detection tools for assisting individuals with avoiding exposure generally require sophisticated technology and expertise. These tools are also typically too bulky for individuals to use at the point of consumption of food.

SUMMARY

In one aspect, a device is provided comprising: a food allergen detection platform comprising: a substrate; and a molecularly imprinted polymer layer in contact with the substrate, the molecularly imprinted polymer layer comprising receptor sites imprinted in a first surface of the polymer, the receptor sites configured to accept a trace molecule of a food allergen; and a non-imprinted polymer layer in contact with the substrate; and a sensor chip comprising the molecularly imprinted polymer and the non-imprinted polymer, which is configured to detect the presence of the trace molecule upon binding to one or more of the receptor sites on the molecularly imprinted polymer.

In some embodiments, the device further includes a processing device, wherein the processing device is configured to communicatively couple to the sensor chip, wherein the processing device is configured to determine a resistance difference between a resistance of the molecularly imprinted polymer layer and a resistance of the non-imprinted polymer layer. In any of the above embodiments, the processing device may determine the presence of the food allergen when the resistance of the molecularly imprinted polymer layer is greater than the resistance of the non-imprinted polymer layer. In any of the above embodiments, the processing may determine the presence of the food allergen when the resistance of the molecularly imprinted polymer layer is less than the resistance of the non-imprinted polymer layer. In any of the above embodiments, the device may also include a reservoir, wherein the reservoir comprises a capsule that encapsulates a solvent; and a chamber for mixing the solvent with food. In any of the above embodiments, the device may further include a locking mechanism for locking the substrate into the chamber. In any of the above embodiments, the locking mechanism may include a ramp adjacent to the reservoir. In any of the above embodiments, the ramp is configured to puncture the capsule releasing the liquid into the reservoir. In any of the above embodiments, the device further comprises a recess configured to house the sensor chip.

DETAILED DESCRIPTION

Figure 1:
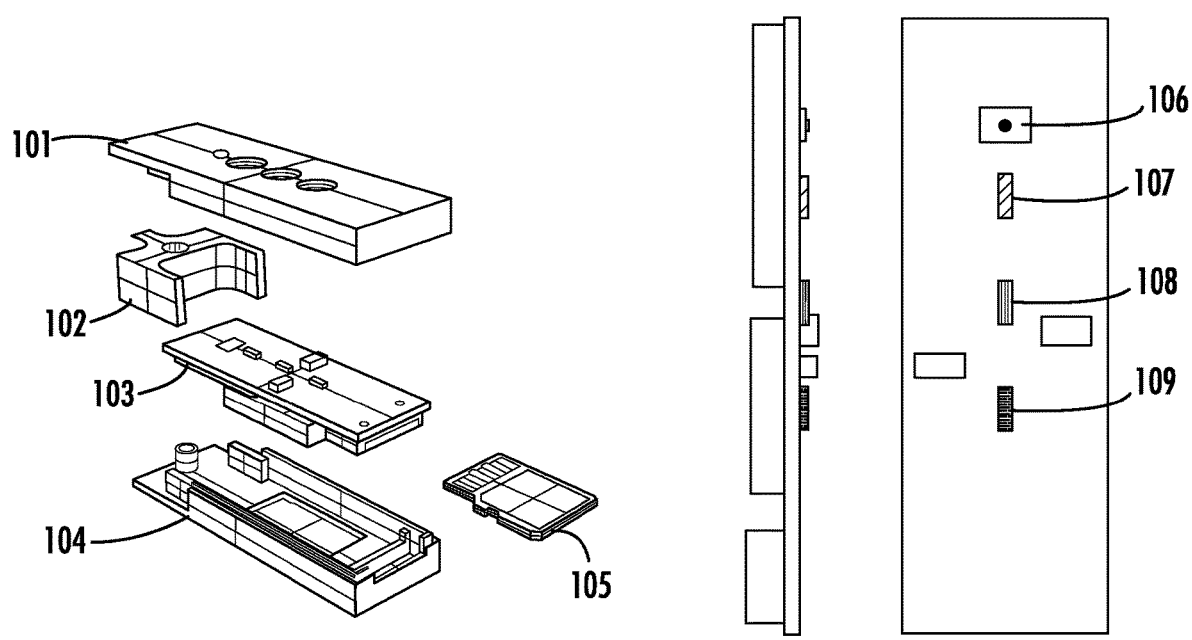
FIG. 1 shows a printed circuit board 1, according to one embodiment.

Eating foods prepared by others can be challenging when you have a food allergy or intolerance. The present technology provides a fast and portable food allergen and/or ingredient detection device enabling users to directly sample their food for unwanted ingredients. The device provides individuals the ability to feel safer about the foods they eat. The food allergen(s) and/or ingredients may be detected by inserting a substrate (e.g., a single-use test strip) into a liquid or solid food sample. The substrate may then be inserted into the chamber of the device, shaken, and connected to a processing device. The device includes a sensor comprising molecularly imprinted polymers. The molecularly imprinted polymers are polymer compositions having synthetic cavities, or binding pockets, designed to bind to target molecules. If the target allergen is present in the liquid or food sample, binding occurs, i.e. the target allergen or a molecule indicative of the target allergen/ingredient fills the binding pocket in the molecularly imprinted polymer, and the processing device then detects a measurable interaction, alerting the user to the presence of the target ingredient within a short period of time (e.g., seconds). If no binding occurs, the processing device signals that the target ingredient was not detected.

The processing device can be configured as a wearable device, or it may be integrated into everyday products that users can keep with them. With an accompanying software application (i.e. "app"), users can track and upload tests, connect with other food-allergic individuals, and store and share important information including, but not limited to, emergency contacts. FIGS. 1 through 11 show illustrative embodiments of the processing device.

Definitions

The following terms are used throughout this disclosure, as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Unless otherwise indicated, numeric ranges, for instance as in "from 2 to 10," are inclusive of the numbers defining the range (e.g., 2 and 10).

Unless otherwise indicated, ratios, percentages, parts, and the like are by weight.

Food Allergens

Food allergens vary in form, chemical makeup, and location within substances consumed by humans. Illustrative consumable substances that may include a food allergen include, but are not limited to, animal products, grains (e.g., gluten), vegetables, fruits, dairy products, fish, beverages, legumes, chocolates, synthetic food chemicals (e.g., monosodium glutamate (MSG), and any combinations of two or more thereof. A consumable substance may include one or more food allergens. In one example, a food allergen may include a food protein. Due to the importance of peanut allergies, a peanut-related food allergen is used in an exemplary fashion in this disclosure. It is contemplated that other food allergens may replace the discussed peanut-related food allergen in the example, embodiment, implementation or other aspect of the disclosure. One way to test for the presence of a peanut-related food allergen is to test for a peanut protein allergen. Examples of a peanut protein include, but are not limited to, arachis hypogaea allergen 1 (ara h1), arachis hypogaea allergen 2 (ara h2), arachis hypogaea allergen 3 (ara h3), and combinations of any two or more thereof.

A food allergen may be present in any of a variety of items that may be a target for detecting a food allergen. For example, a food allergen target item may be a food itself (or a portion thereof) or an item that the food has come into contact with (e.g., a serving utensil, a table, etc.). Food allergen target items may come in a variety of forms including, but not limited to, a solid, a liquid, a gas, a suspension, and any combinations thereof. Example solid food allergen target items include, but are not limited to, a solid food (e.g., a bread, a nut), a plate, a table, a utensil, and any combinations thereof. Example liquid food allergen target items include, but are not limited to, a liquid food, a beverage (e.g., a soda, milk, a juice), a food extract, and any combinations thereof. Examples of a suspension food allergen target item include, but are not limited to, an allergen suspended in air (e.g., a food allergen in particulate form), an allergen suspended in water, and any combinations thereof. Further specific example of common food allergens are listed in Table 1 below.

TABLE 1

| List of allergens: |
|---|
| Almond |
| Almond paste |
| Anacardium nuts |
| *Anacardium occidentale* (Anacardiaceae) [botanical name, Cashew] |
| Artificial nuts |
| Beech nut |
| Brazil nut |
| *Bertholletia excelsa* (Lecythidaceae) [botanical name, Brazil nut] |
| Bush nut |
| Butternut |
| *Butyrospermum Parkii* [botanical name, Shea nut] |
| *Canarium ovatum Engl.* in A. DC. (Burseraceae) [botanical name, Pili nut] |
| Caponata |
| *Carya illinoensis* (Juglandaceae) [botanical name, Pecan] |
| *Carya* spp. (Juglandaceae) [botanical name, Hickory nut] |
| Cashew |

TABLE 1-continued

List of allergens:

*Castanea pumila* (Fagaceae) [botanical name, Chinquapin]
*Castanea* spp. (Fagaceae) [botanical name, Chestnut (Chinese, American, European, Seguin)]
Chestnut (Chinese, American, European, Seguin)
Chinquapin
*Cocos nucifera L.* (Arecaceae (alt. Palmae)) [botanical name, Coconut]
*Corylus* spp. (Betulaceae) [botanical name, Filbert/hazelnut]
Filbert
*Fagus* spp. (Fagaceae) [botanical name, beech nut]
Gianduja
Ginko nut
*Ginkgo biloba L.* (Ginkgoaceae) [botanical name, Ginko nut]
Hazelnut
Heartnut
Hickory nut
Indian nut
*Juglans cinerea* (Juglandaceae) [botanical name, Butternut]
*Juglans* spp. (Juglandaceae) [botanical name, Walnut, Butternut, Heartnut]
Karite (shea nut)
Lichee nut
*Litchi chinensis Sonn. Sapindaceae* [botanical name, Lichee nut]
Lychee nut
Macadamia nut
*Macadamia* spp. (Proteaceae) [botanical name, Macadamia nut/Bush nut]
Mandelonas
Marzipan
Mashuga nuts
Nangai nuts
Natural nut extract (for example, almond extract)
Nougat
Nu-Nuts ®
Nut butters (e.g., Almond butter, Hazelnut butter, Brazil nut butter, Macadamia nut butter, Pistachio nut butter, Shea nut butter, Karike butter, as well as other nut butters)
Nut meal
Nutella ®
Nutmeat
Nut oil (e.g., Walnut oil as well as other nut oils)
Nut paste
Nut pieces
Pecan
Piñolia
Pili nut
Pine nut
Pine nut (Indian, piñon, pinyon, pigndi, piñolia, pignon nuts)
Pinon nut
Piñon or Piñon nut
*Pinus* spp. (Pineaceae) [botanical name, Pine nut/piñon nut]
Pistachio
*Pistacia vera L.* (Anacardiaceae) [botanical name, Pistachio]
Pralines
*Prunus dulcis* (Rosaceae) [bontanical name, almond]
Shea nut
Sheanut
*Vitellaria paradoxa C.F. Gaertn.* (Sapotaceae) [botanical name, Shea nut]
Walnut (English, Persian, Black, Japanese, California)

A Food Allergen Detection Device

To enable convenient detection of the above listed food allergens, the technology provided herein is a food allergen detection device that may be wearable. The device includes a food allergen detection platform having a substrate and a molecularly imprinted polymer layer in contact with the substrate, the molecularly imprinted polymer layer including receptor sites imprinted in a first surface of the polymer, the receptor sites configured to accept a trace molecule of a food allergen, and the receptor sites having been formed with a template molecule; and a non-imprinted polymer layer in contact with the substrate; and a sensor chip comprising the substrate, the molecularly imprinted polymer and/or the non-imprinted polymer, which is configured to detect the presence of the trace molecule upon binding of one or more trace molecules to one or more of the receptor sites on the molecularly imprinted polymer.

Figure 19:
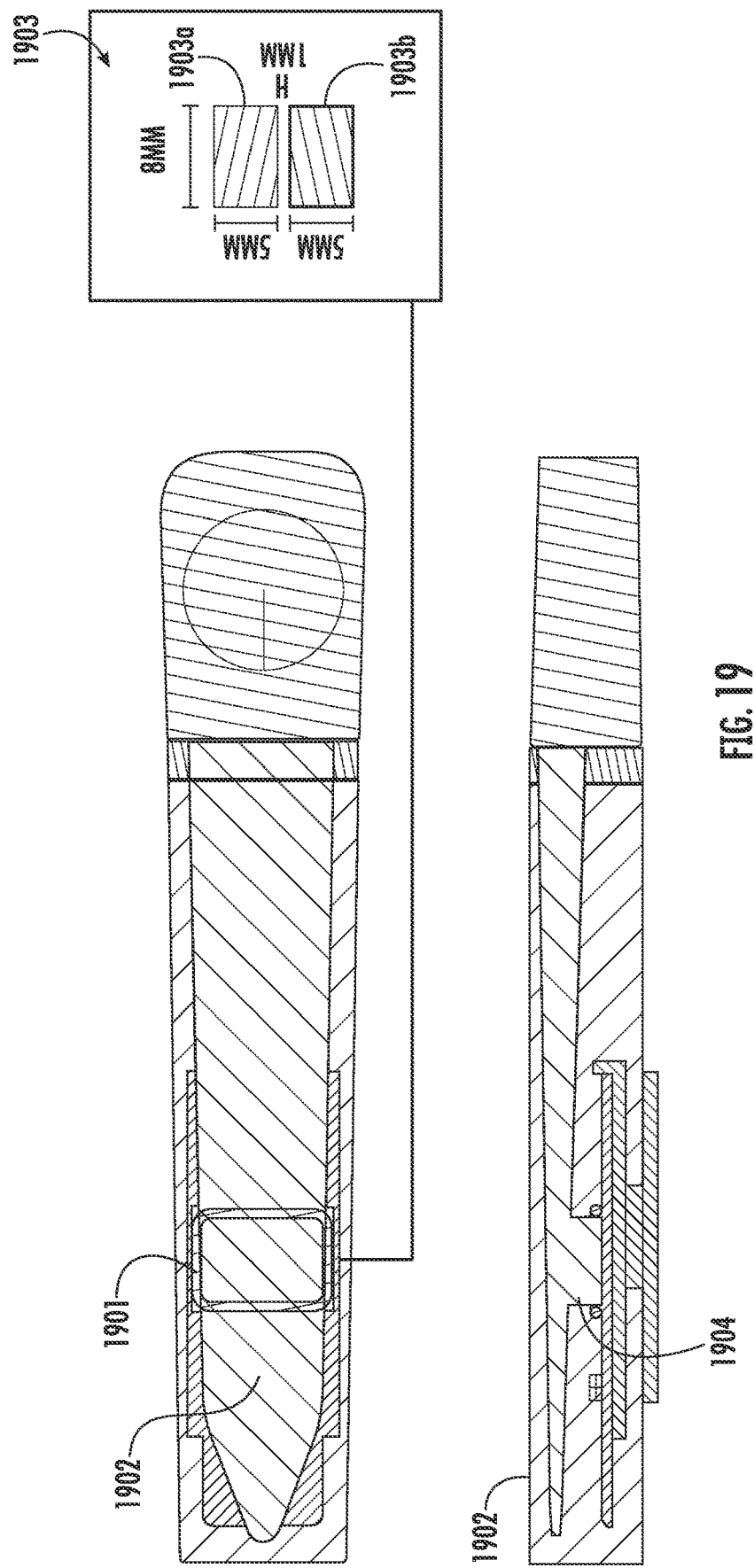
FIG. 19 shows overhead and sideview of the device with a detector for food allergen detection, according to one embodiment.
Figure 20:
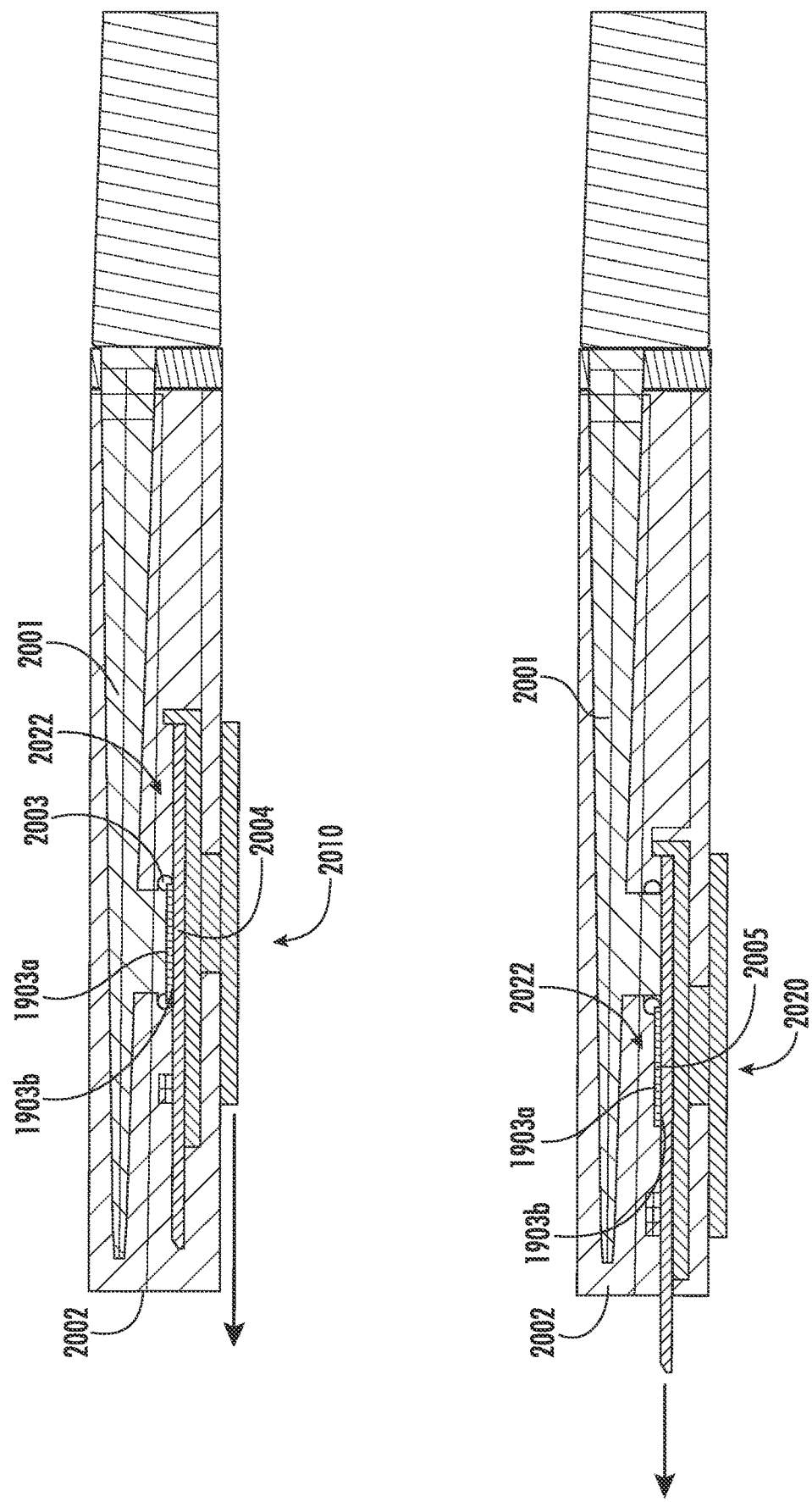
FIG. 20 shows overhead view of the device with a detector for food allergen detection, according to one embodiment.

In one aspect, the present technology provides a device including a sensor comprising a printed circuit board comprising a chip comprising a molecularly imprinted polymer (MIP) and a non-imprinted polymer (NIP); a reservoir comprising a liquid; and a chamber for mixing the liquid with a food. In one embodiment, a body surrounds at least partially the sensor, the reservoir, and the chamber of the device. Referring to FIG. 19, a body 1902 surrounds the printed circuit board with the MIP (1903*a*) and NIP (1903*b*) chips (collectively 1903), located within the body of the device at 1901 (overhead view) or 1904 (sideview). FIG. 20 shows the same embodiment of the device as FIG. 19, wherein the substrate strip 2001 is inserted into the sheath 2002, wherein the printed circuit board 2004 is enclosed by an O-ring 2003. FIG. 20 further shows an embodiment of the device, wherein the printed circuit board holder has been pulled out and the printed circuit board 2005 is outside the O-ring 2003 for drying after having been exposed to a liquid food sample. The MIP and NIP chips (1903*a* and 1903*b*) are movable in FIG. 20 from a first position 2010 to a second position 2020 during the pulling out of the circuit board 2005.

Figure 12:
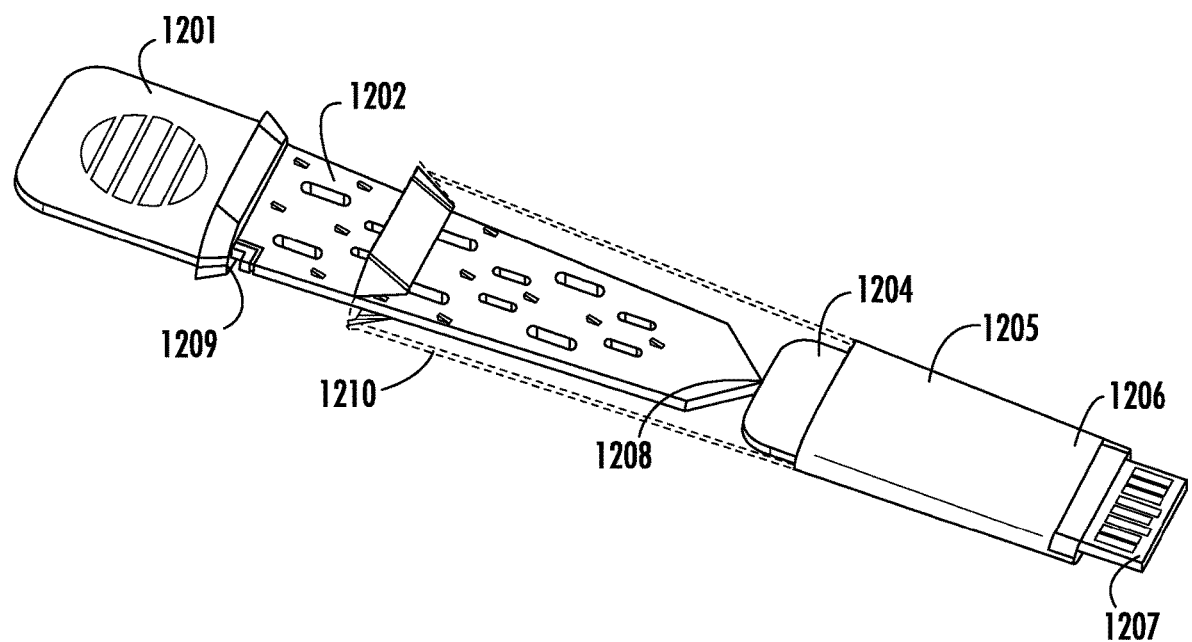
FIG. 12 shows the outside view of a device for food allergen detection, according to one embodiment.
Figure 13:
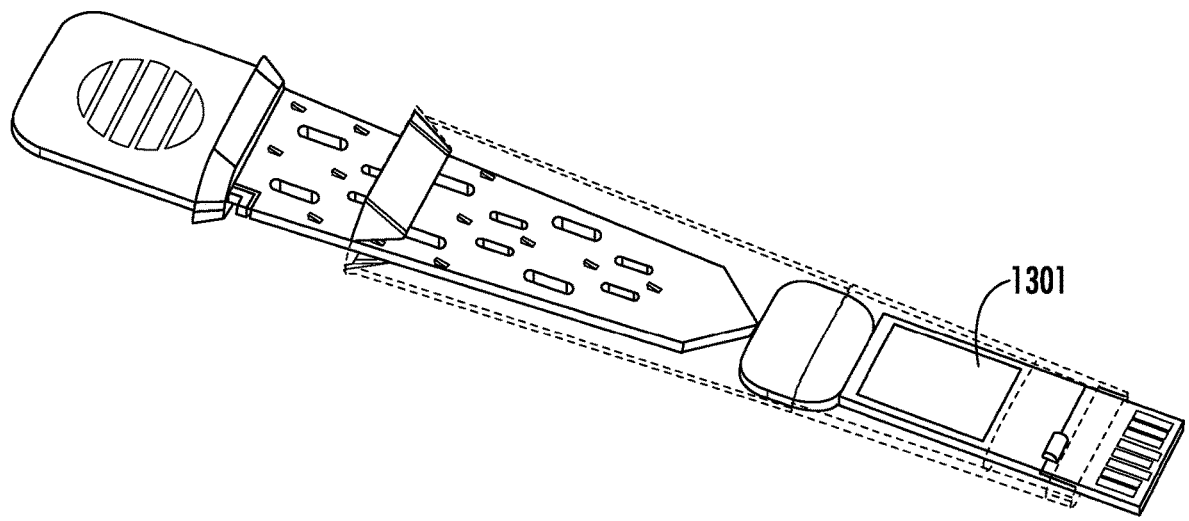
FIG. 13 shows the inside view of a device for food allergen detection, according to one embodiment.
Figure 14:
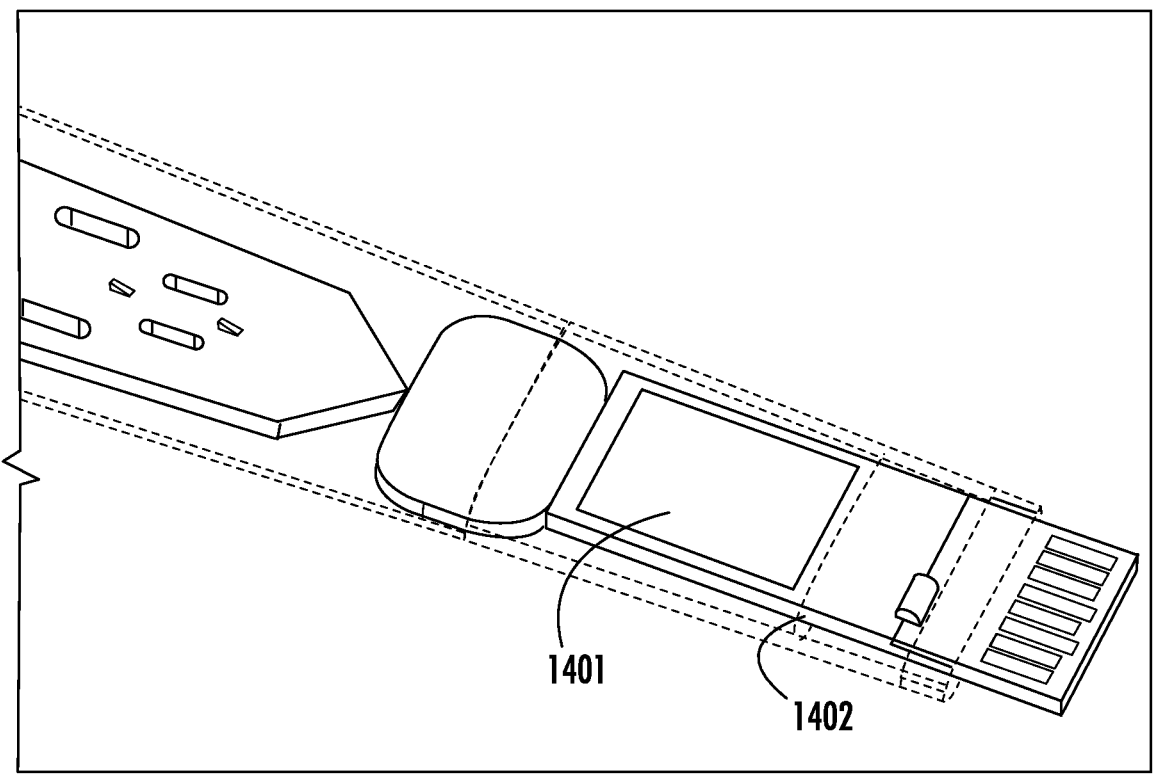
FIG. 14 shows the inside view of a device for food allergen detection with annotation, according to one embodiment.
Figure 15:
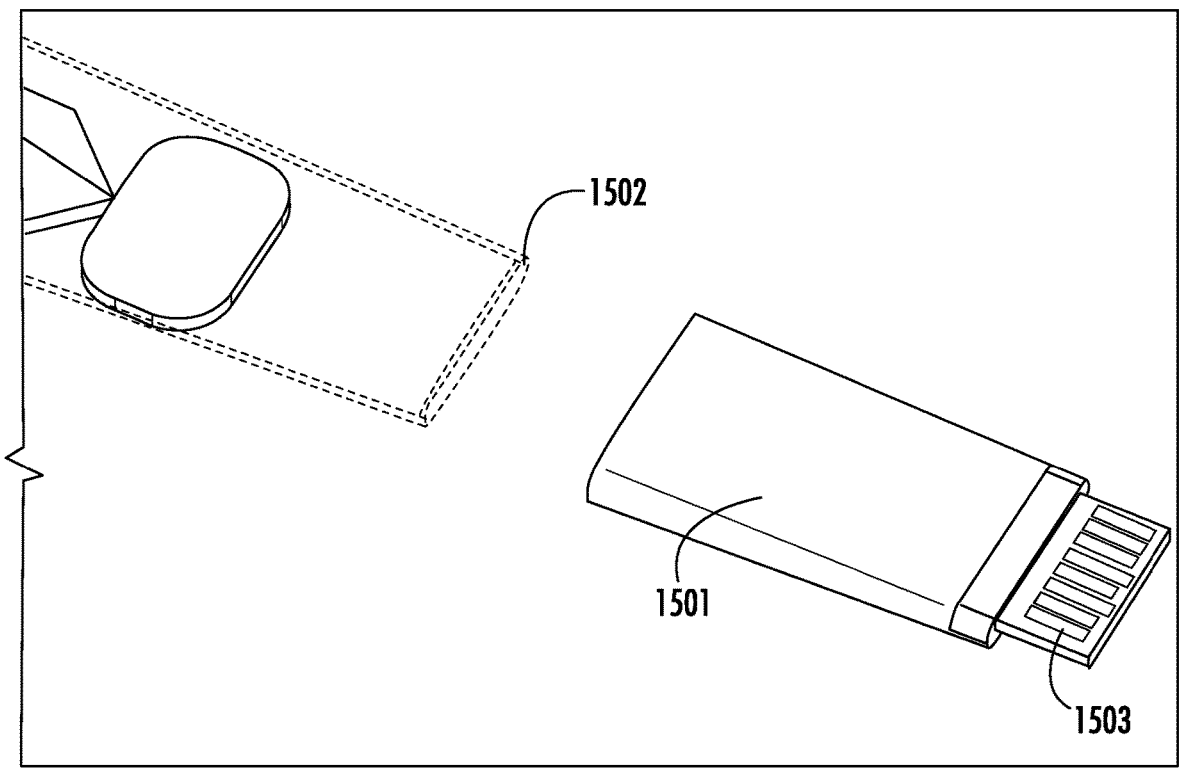
FIG. 15 shows the inside view of a device for food allergen detection with annotation, according to one embodiment.
Figure 16:
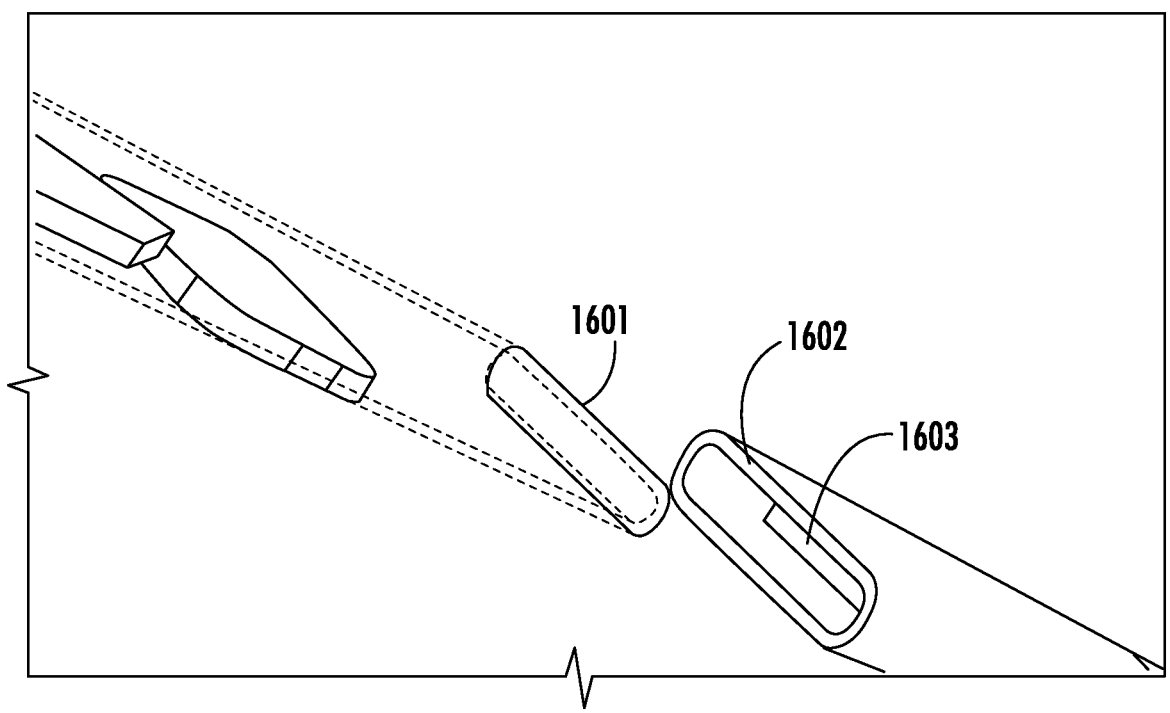
FIG. 16 shows the inside chamber of a device for food allergen detection, according to one embodiment.

In some embodiment, the body is configured to receive a substrate with the food on a surface of the substrate. In further embodiments, the reservoir comprises a capsule that encapsulates the liquid. In yet further embodiments, the liquid comprises a solvent. In some embodiments, the solvent comprises water. In some embodiments, the liquid comprises a buffer. In some embodiments, the device further comprises a locking mechanism for locking the substrate into the chamber. FIG. 12 shows an illustrative embodiment of a device with a locking mechanism that can lock the substrate into a chamber. Referring to FIG. 12, the substrate may be a single molded strip 1201 that includes channels for capillary action on liquids and cheese grater to capture hard/dry food 1202. The sheath may have an overmolded rubber that seals against strip when completely inserted into the sheath 1203. The sheath of FIG. 12 may contain a plastic pouch 1204 filled with a solvent buffer. Upon insertion of the substrate strip into this sheath, the substrate strip punctures the plastic pouch with a pointed tip 1208 and the solvent is released and mixes with the food samples. FIG. 12 also illustrates how a locking mechanism 1209 may ensure seal and prevent reuse. After mixing the food sample with the solvent, the food sample may be exposed to the printed circuit board inside the printed circuit board holder 1206. The printed circuit board terminates in a MicroSD connector 1207 for insertion into the Amulet processing device. FIG. 13 shows inside view of the device and the printed circuit board 1301 inside the device. FIG. 14 shows the exposed film 1401 containing the MIP and NIP sensor. Referring to FIG. 14, when the printed circuit board holder is pulled out, rubber sheets 1402 with slit at the end of the sheath will dry off the printed circuit board. Referring to FIG. 15, when the printed circuit board holder 1501 is pulled, rubber sheets 1502 will dry of the printed circuit board before connecting it to the Amulet processing device via the MicroSD connector 1503. Referring to FIG. 16, the printed circuit board may be wiped dry by flat rubber sheets 1601 by having the printed circuit board holder 1602 go outside the sheath and the printed circuit board 1603 goes inside the sheath. In another embodiment, the solvent may be released by a ramp. In some embodiments, the ramp is adjacent to the reservoir. In some embodiments, the compression of the ramp punctures the capsule releasing the liquid into the reservoir. Referringto FIG. 17, a ramp 1701 may be pushed down by the insertion of a substrate strip 1704 into the sheath 1705.

Figure 18:
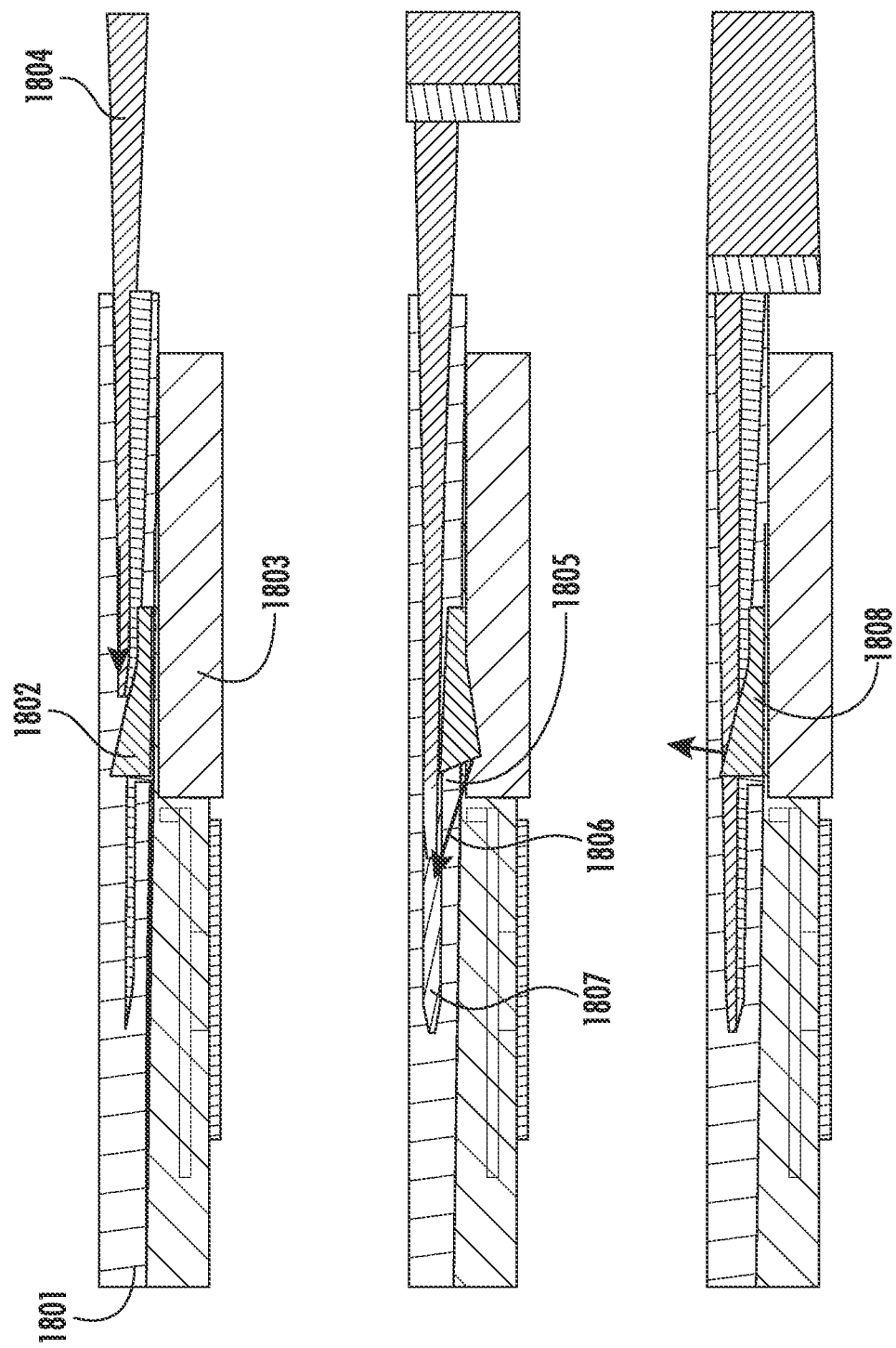
FIG. 18 shows the overhead view of a device with a ramp and depicts how inserting strip into the sheath releases water to the chamber, according to one embodiment.

The solvent such as water is then released from the chamber 1703 under the ramp, and the solvent flows over the printed circuit board 1702. FIG. 18 illustrates in another embodiment how inserting the substrate strip 1804 into a sheath 1801 pushes down a ramp 1802 to release a solvent from a chamber 1803 by breaking a seal 1805, resulting in that a solvent 1806 flows into a reservoir 1807. FIG. 18 also illustrates how the ramp 1802 may function to lock the strip in place 1808.

In another embodiment, the device comprises a recess 2022 configured to house the sensor. In some embodiments, the recess has a first portion for housing the sensor in a first position 2010 and a second portion for housing the sensor in a second position 2020, the first and the second portions being linked such that the sensor is moveable from the first position 2010 to the second position 2020 in the recess 2022. In some embodiments, when in the first position 2010 the chip is in contact with the reservoir. In some embodiments, when in the second position 2022 the chip is not in contact with the reservoir. In some embodiments, when in the second position 2020 a portion of the printed circuit board is outside of the body. In some embodiments, the device further comprising an access port communicating with the recess 2022 for manual movement of the sensor between the first 2010 and second 2020 positions. In some embodiment, the sensor comprises the NIP 1903b and the MIP 1903a of the device. In further embodiments, the NIP 1903b comprises a film. In some embodiment, the MIP 1903a comprises a film. FIGS. 19 and 20 show an illustrative embodiment of the device with a sensor comprising the MIP 1903a and NIP 1903b inside the housing.

In some embodiments, the MIP of the device comprises receptor sites for a food allergen. In further embodiments, the food allergen comprises a molecule with a molecular weight less than about 5000 g/mol. In yet further embodiments, the food allergen comprises a peanut allergen, tree nut allergen, milk allergen, egg allergen, wheat allergen, soy allergen, meat allergen, fish allergen, shellfish allergen, coconut allergen, or a combination of two or more thereof. In other embodiments, the food allergen comprises a nut allergen listed in Table 1. In some embodiments, the tree nut allergen comprises almond, almond paste, or a combination thereof. In some embodiments, the food allergen comprises a soy allergen. In some embodiments, the food allergen comprises a flavonoid, amygdalin, or a combination thereof. In further embodiments, the flavonoid comprises an isoflavonoid, neoflavonoid, or derivatives thereof. In yet further embodiments, the isoflavonoid or derivative thereof comprises isoflavones, isoflavonones, isoflavans, pterocarpans, rotenoids, or combinations of two or more thereof.

The substrate of the device is a strip or a pin that is exposed to food. Accordingly, in some embodiments, the device further comprises a substrate. In some embodiments, the substrate comprises glass, plastic, paper, quartz, alumina, mica, silicon, a III-IV semiconductor compound, or combinations of two or more thereof. In some embodiments, the substrate has an elongated shape. FIGS. 12-16 show an illustrative embodiment of a substrate with elongated shape. In some embodiments, the substrate has a top and a bottom. In some further embodiments of the substrate, the bottom has a tapered end and/or the top has a portion for holding the substrate. In other embodiments, the substrate comprises one or more holes and/or cervices. In yet other embodiments, the device of any one of paragraphs, the substrate is disposable. In yet further embodiments, the substrate is recyclable. In some embodiments, the substrate further comprises a wireless transceiver.

Food exposed on the substrate may contact the sensor chips directly or may be mixed with one or more different solvents first. The solvent or solvents may be stored in compartments, capsules, or pouches inside the disposable unit. The solvents may be used to solubilize solid tracer molecules or to extract the tracer molecule from an oil or food matrix. Alternatively, a solvent may be used to reduce the solubility of a tracer molecule, altering the equilibrium between being dissolved in the solvent and bound to the imprinted polymer. Solvents may include water, aqueous buffer, saline solutions, ethanol, other organic solvents, or any combination thereof. In one embodiment, mild alkaline buffer solution (pH ~9-11 carbonate/ bicarbonate) is used to dissolve and extract the tracer molecule (genistein) from solid foods. Salt (for example potassium chloride) is mixed in to modulate solubility, encouraging selective binding of the tracer molecule to the imprinted polymer film.

The sensor chips may be stored in a dry compartment within the disposable or in in a compartment containing solvent. Dry chemicals may also be mixed with the food sample to modulate the solubility of the target tracer molecules. These chemicals may include buffers, salts, and surfactants, and they may be stored in the same chamber of the disposable as the sensor chips or in a separate chamber.

Figure 17:
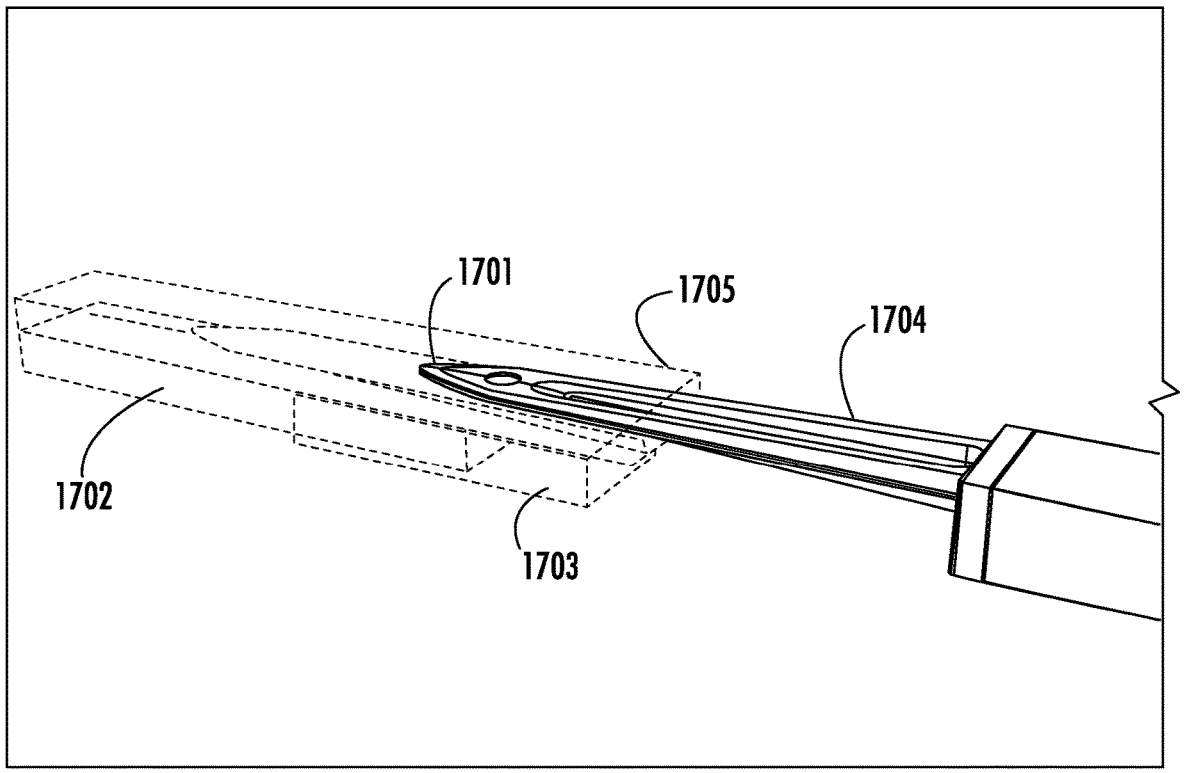
FIG. 17 shows the overhead view of a device with a ramp, according to one embodiment.

The substrate may be constructed of a glass, a plastic, a paper, quartz, alumina, mica, silicon, a Groups III-IV semiconductor compound, or a combination of any two or more thereof. The substrate is then inserted into the device, wherein this insertion results in puncturing of a capsule containing a solvent that extracts a trace molecule of a food allergen from the food sample. As used herein, the term "a trace molecule of a food allergen" or just "trace molecules" refers to molecules that are suitable for detecting the presence of an allergen but may not necessarily be allergens themselves. The device may also include a reservoir, wherein the reservoir includes a capsule that encapsulates a solvent; and a chamber for mixing the solvent with food. The device may also include a locking mechanism for locking the substrate into the chamber. Such locking mechanisms may include a ramp adjacent to the reservoir, wherein compression of the ramp punctures the capsule, and wherein the solvent is released into the reservoir. An illustrative embodiment of the device with a ramp is shown in FIGS. 17 and 18.

Insertion of the substrate into the device also brings the food and solvent mixture in contact with a molecularly imprinted polymer ("MIP"). MIPs may be utilized in systems and methods for detecting the presence of food allergens, and a non-imprinted polymer (NIP) may be used as a negative control.

The molecularly imprinted polymers may be manufactured by methods known to those of skill in the art including those provided in PCT/US2014/048676, U.S. patent application Ser. Nos. 14/624,813, 14/342,059, 14/407,860, 14/065,990, and U.S. Pat. No. 9,429,536, all of which are herein incorporated by reference. Examples 1-3 herein illustrate the synthesis of MIPs. In general, MIPs are synthesized by combining host molecules (functional monomers/polymers) with a "template molecule." As used herein, the term "template molecule" refers to trace molecules of food allergen that can be used to create receptor sites in a polymer. Template molecules are trace molecules with features such as hydrogen bond donors, hydrogen bond acceptors, and pi electron systems that are useful to create unique receptor sites. Solubility in an aqueous or organic solvent system for extraction from solid foodstuff is another useful attribute in a template molecule. In some embodiments, the template molecule of the first food allergen is an organic molecule. In some embodiments, the organic molecule has a molecular weight of less than about 900 Daltons, less than about 800 Daltons, less than about 700 Daltons, less than about 600 Daltons, less than about 500 Daltons, less than about 400 Daltons, less than about 200 Daltons, less than about 100 Daltons. In some embodiments, the organic molecule has a molecular weight of less than about 500 Daltons. The template molecule may be amygdalin, apigenin-6-arabinoside-8-glucoside,apigenin-6-glucoside-8-arabinoside, arachin, biochanin A, catechin gallate, crysoeriol, cyanocobalamin, daidzein, daidzin,5-5'-dehydrodiferulic acid, 5-8'-dehydrodiferulic acid, 5,7-dihydroxychromone, 5,7, dimethoxyisoflavone, ferulic acid, galactose, genistein, genistin, 3-hydroxybiochanin A, isochlorogenic acid, isoferulic acid, juglone, lactose, lariciresinol, medioresinol, procyanidin B2, procyanidin C1, resveratrol, resveratrol 3-glucoside, secoisolariciresinol, syringaresinol, syringic acid, trans-sinapic acid. In other embodiments, the template molecule is a larger organic molecules such as a polypeptide, epitope, aptamer, or protein.

By combining template molecules with polymers, a cavity remains in the polymer after removing the template molecules. The cavities complement the template molecule in size, shape, and chemical functionality. The cavities form the receptor sites for the indicator molecules of food allergens. Thus, the MIPs are solid or gel-phase polymers which were synthesized or deposited in the presence of a template molecule. Accordingly, a process of making a molecularly imprinted polymer for detecting a food allergen, comprises (1) combining a monomer, a template molecule, and a cross-linker into a mixture; and (2) initiating polymerization of the mixture. In some embodiments the monomer comprises a poly(4-vinylphenol), a poly(urethane), a poly(methylmethacrylate), a poly(methacrylic acid), poly(hydroxyethylmethacrylate), poly(vinylpyrrolidone), a co-polymer of any two or more there, or a polymer blend of any two or more thereof. In some embodiments, the cross-linker comprises ethylene glycol dimethacrylate, trimethylopropane trimethacrylate (TRIM), divinylbenzene, methylene bisacrylamide. In some embodiments, the initiating polymerization step is performed by adding a radical initiator such as azobisisobutyronitrile. Initiating polymerization may also be performed by reversible addition-fragmentation chain-transfer polymerization or catalyzed polymerizations by using olefin metatheses procedures such as ring opening metathesis polymerization (ROMP).

In some embodiment the polymer is a non-cross-linked polymer.

NIPs are synthesized with the same processes as MIPs but without the template molecules.

The selective binding capabilities of the MIPs can be measured by incubating them in a solution of the tracer molecule and measuring how much binding occurs. Binding measurement can be done spectroscopically by either UV-vis of the remaining tracer molecule in solution or FTIR-ATR of the polymer itself. Binding behavior of the MIPs is compared with the non-imprinted polymers. Methods of detecting binding in such systems include direct measurement of the film to observe the incorporation of bound target molecule, or measuring the remaining target molecule in solution to indirectly measure binding. These measurements may be taken before and after incubation, continuously, or with some degree of mid-incubation datapoints, and may include UV, UV-visible, visible, infrared, near infrared, raman, or nuclear magnetic resonance spectroscopy, high pressure liquid chromatography (HPLC), or gas chromatograph—mass spectrometry, among others.

MIPs and NIPs are then used to manufacture a sensor chip for detecting food allergen based on binding of the trace molecules to the complementary cavities created by the template molecules. Example 1 illustrates the process of making a sensor chip.

Figure 21:
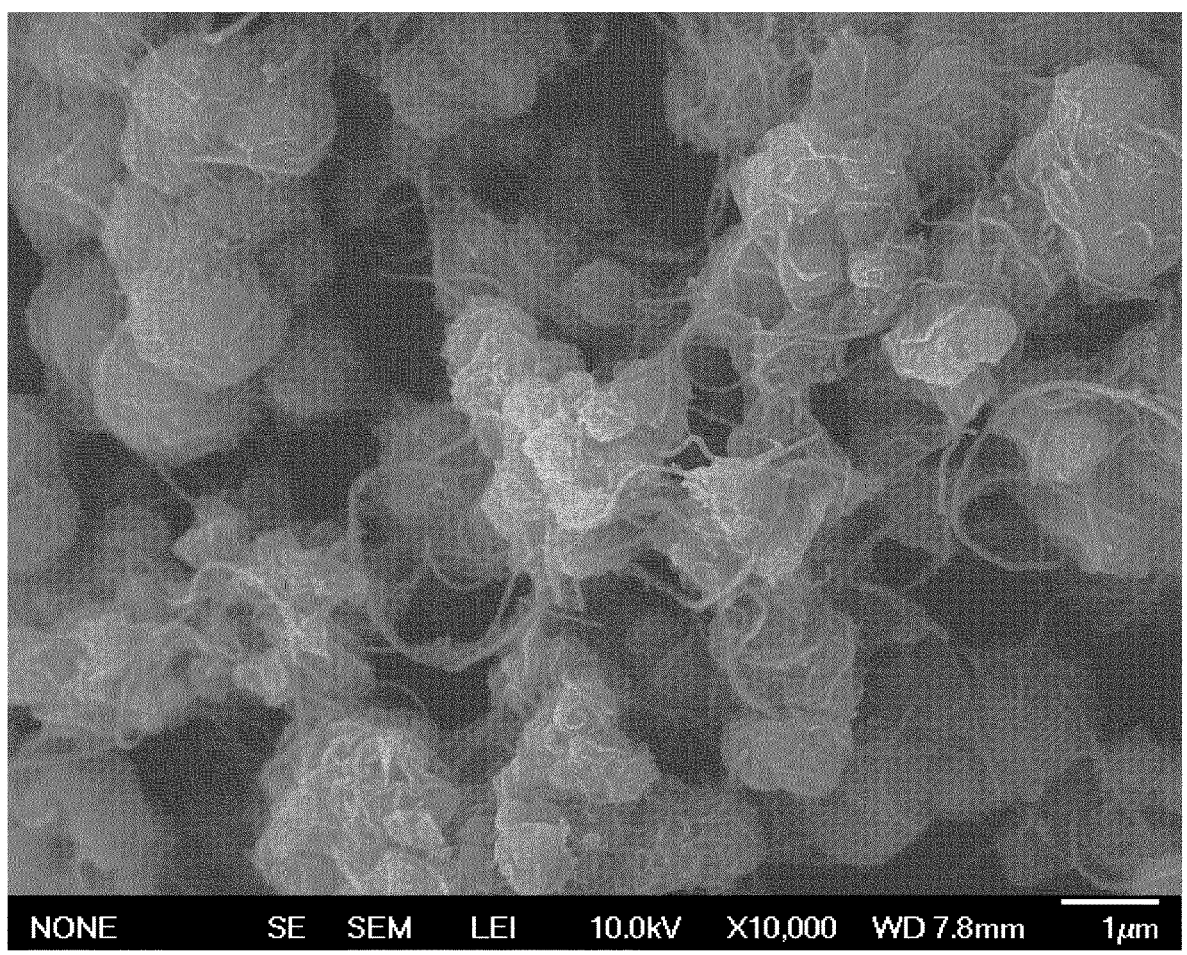
FIG. 21 shows scanning electron microscopy picture of multi walled carbon nanotubes (MWCNT) wrapped around polymer nanoparticles at 10,000× magnification, according to one embodiment.
Figure 22:
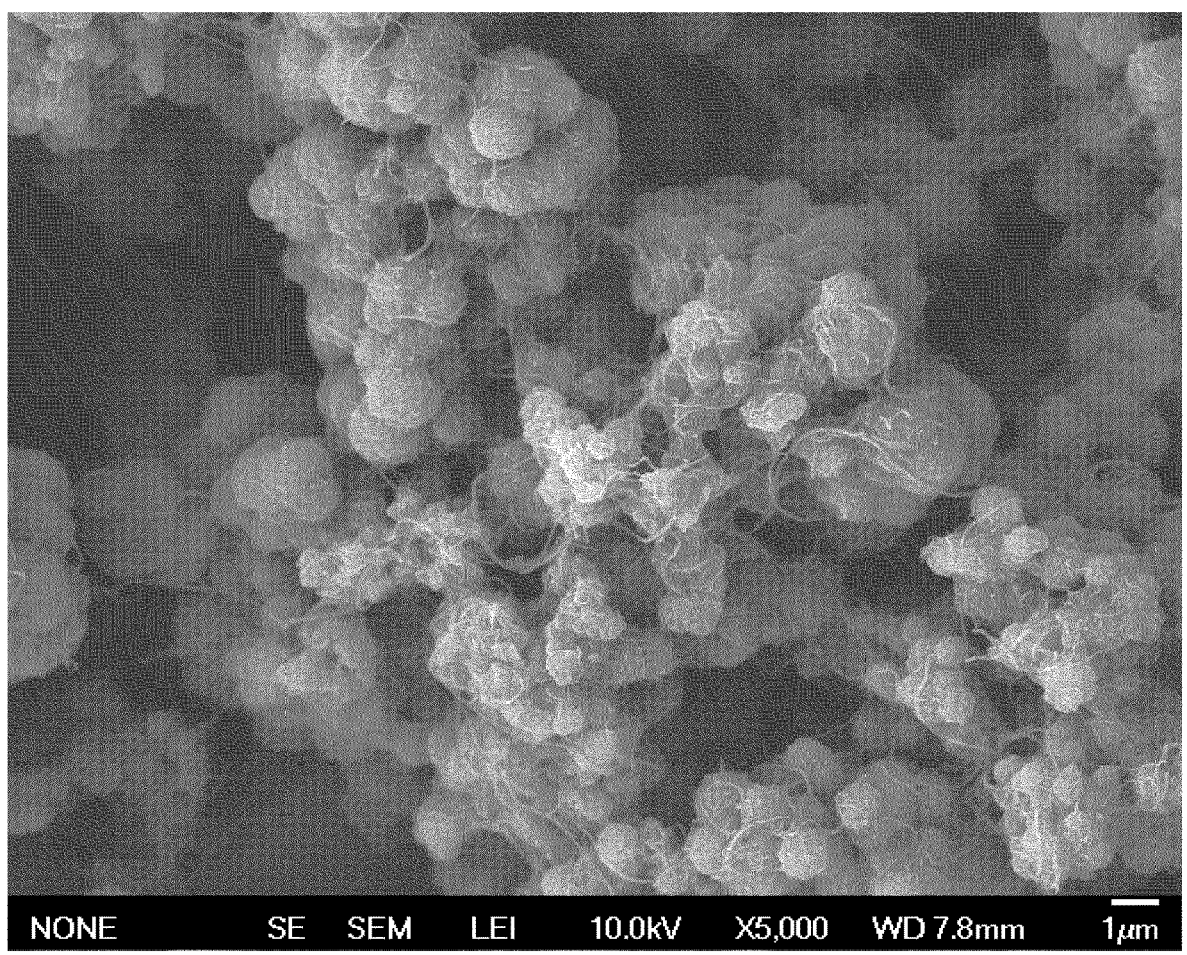
FIG. 22 shows scanning electron microscopy picture of multi walled carbon nanotubes (MWCNT) wrapped around polymer nanoparticles at 5,000× magnification, according to one embodiment.

Manufacturing a sensor chip with an MIP and a NIP film requires that the MIPs and NIPs have some electrical characteristics. The MIPs and NIPs are made to be electrically conductive by wrapping them with multi-wall carbon nanotubes (MWNT). FIGS. 21-22 illustrate MWNT wrapped MIPs. In other embodiments, the conductive materials may be graphene or graphite nanoplatelets, carbon black, single wall carbon nano-tube (SWCNT), double-wall (DWCNT), or other sizes of multi-walled nanotubes (anywhere from ~8 to 200 nm in diameter). Functionalized SWCNT or MWCNT, having functional groups such as, but not limited to, —OH, —NH$_2$, —F, —C(O)OH, or =O on the surface may also be used. These various carbon nanotubes may be of any length, or typically from about 1 to about 50 μm. Alternatively, conductive polymer such as (polyaniline, polypyrrole poly(o-toluidine), polythiophene, poly(3,4-ethylenedioxythiophene) ("PEDOT"), and the like) may be used to provide the composite film the desired conductivity. Alternatively, inorganic nanowires may be used to give the composite the desired conductivity. Casting of the MIPs and NIPs as a film on a sensor chip allows detection of changes in electrical resistance.

The films cast on the sensor chips are composed of MIP nanoparticles, multi-walled carbon nanotubes (typical diameter 50-85 nm length 10-15 μm), and a soluble anchor polymer binder such as poly(4-vinylphenol) (typical molar mass 25k Daltons). Poly(4-vinylphenol) may be used as an "anchor polymer" to bind the MWCNT and the polymers to the surface of the sensor chip. Such binding may be accomplished by dissolving the anchor polymer a solvent such as ethanol, adding MWCNTs to the solution (ratio of 1-20% by weight to polymer OR ratio of 6-16% MWCNT by weight to polymer), and sonicating with a tip sonicator for one hour to generate a stable dispersion. The nanoparticles may be added (weight ratio of 1:1-10:1 relative to the nanotubes), the mixture vortexed, and then sonicated with a bath sonicator for 10 minutes.

Polyvinylphenol may be used as an "anchor polymer" to bind the MWCNT and the nanoparticles to the surface of the sensor chip. Anchor polymers may be any suitable soluble polymer for binding of the nanoparticle and conductive material to the surface of the sensor chip. In some embodiments the anchor polymer is nylon-6, polyallylamine, poly (acrylamide), poly(dimethylsiloxane), poly(hydroxyethylmethacrylate), poly(methylmethacrylate), poly (vinylpyridine), poly(methacrylic acid), poly(styrene), poly (vinylpyrrolidone), or any combination or copolymer of any two or more of the above. The anchor polymer may be dissolved in a solvent, for example ethanol, followed by the addition of MWCNT to the solution (at a ratio of about 1 to about 20 wt % to the polymer) and the mixture sonicated with a tip sonicator for one hour to generate a stable dispersion. Nanoparticles may be added (at a weight ratio of 1:1 to 10:1 relative to the nanotubes), the mixture is vortexed, and then sonicated with a bath sonicator for 10 minutes.

Other components of the material that interfaces with the electrical component of the sensor chip may be a binder (such as soluble non-conductive polymers), surfactants, conductive or semiconductive polymers (polyaniline, polypyrrole poly(o-toluidine), etc.) or conductive or semiconductive carbonaceous materials such as carbon nanotubes, graphene nanoplatelets, or carbon black.

Figure 2:
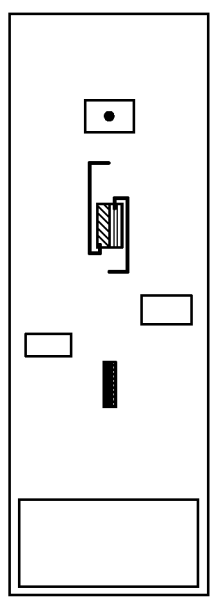
FIG. 2 shows a printed circuit board 2, according to one embodiment.
Figure 3:
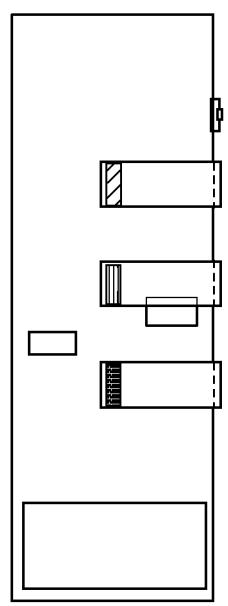
FIG. 3 shows a printed circuit board 3, according to one embodiment.

The circuit boards used as sensor chips may be copper on a PCB material in an interdigitated pattern. In some embodiments, the copper may be laminated on one or both sides of the PCB material. A non-limiting example of PCB material is FR4. These circuit board may roughly be 1 $cm^2$ in area and have an interdigit spacing of 300 µm. FIGS. 1-3 show illustrative example of circuit boards. The mixture of anchor polymer, MWCNTs, and nanoparticles may be aliquoted and spin-cast onto the chip. After spin casting, the chips are baked and stored dry. In some embodiments, the sensor chips are made by film printing, ink-jet printing, drop casting, or blade spreading may be used in place of spin casting. The sensor chip may take any reasonable size and pattern for measuring the resistance of a polymer sample. The insulating substrate and conductive leads may be made of any appropriate materials (chrome/silver/gold/carbon on glass, bakelite etc.). Example 4 illustrates that the MWCNTs made the film conductive, and that the resulting sensor chips could be used for a 2-point resistance measurement.

The sensor chips may be designed to measure any useful electronic properties of the functional material; 2-point resistance measurements, 4-point resistance measurements, conductivity, capacitance etc. Electrochemical means such as cyclic voltammetry or amperometry may also be used.

Figure 4:
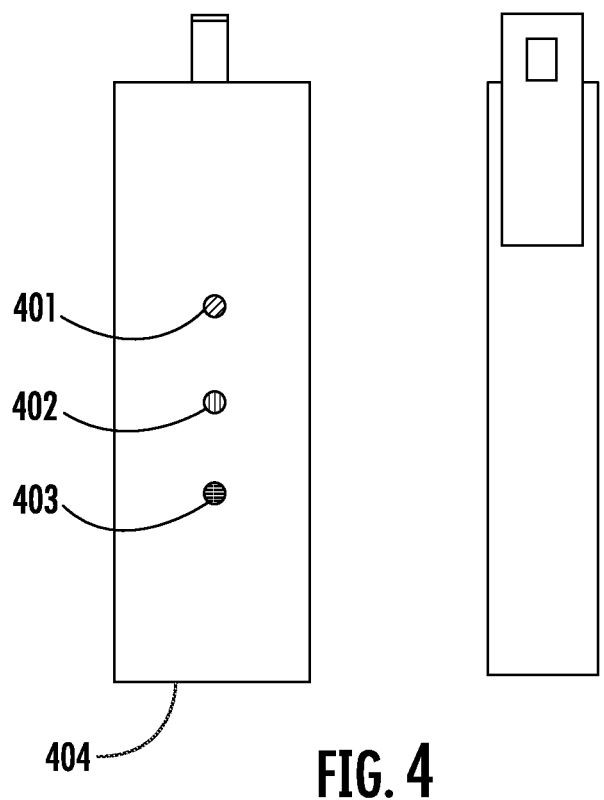
FIG. 4 shows a processing device 1, according to one embodiment. Green, red, and yellow lights are provided to reveal the results of the food allergen test. Green light shows the absence of the food allergen. Red light shows the presence of the food allergen. Flashing yellow light shows that reading is in progress, and a stable yellow light represent an inconclusive reading.
Figure 5:
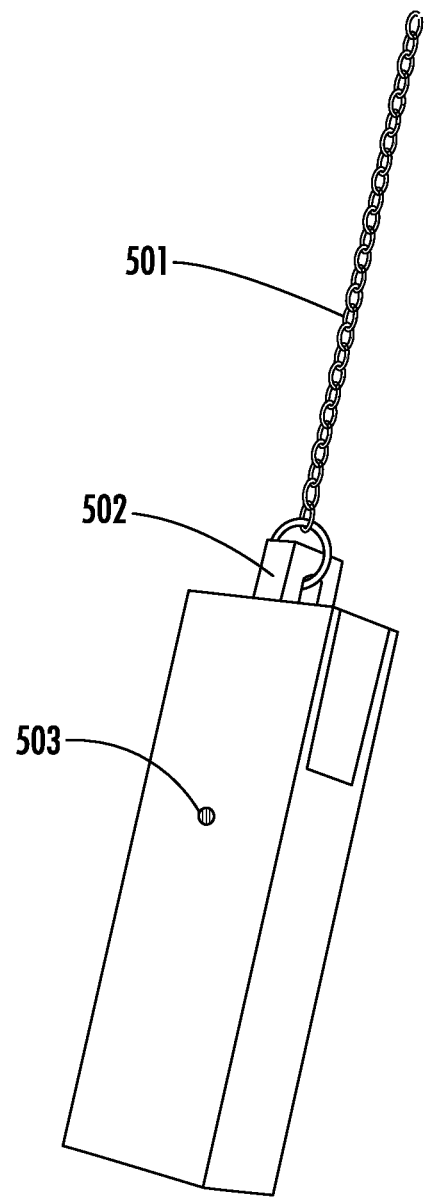
FIG. 5 shows a wearable processing device 1, according to one embodiment.
Figure 6:
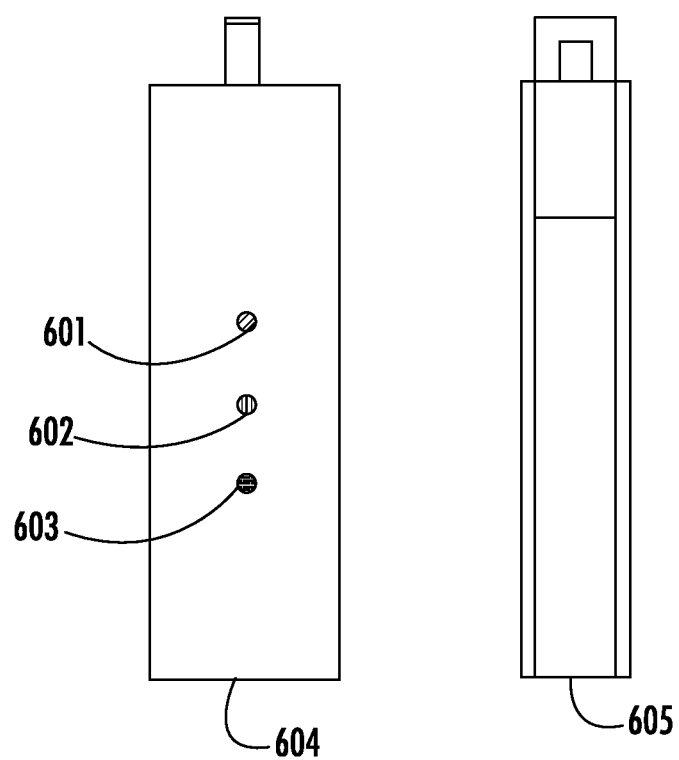
FIG. 6 shows a processing device 2, according to one embodiment. Green, red, and yellow lights are provided to reveal the results of the food allergen test. Green light shows the absence of the food allergen. Red light shows the presence of the food allergen Flashing yellow light shows that reading is in progress, and a stable yellow light represent an inconclusive reading.
Figure 7:
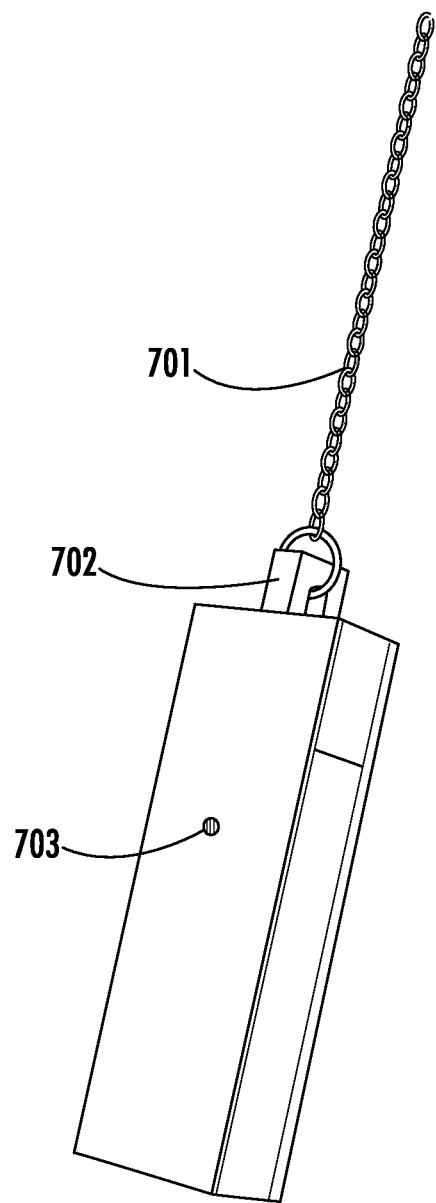
FIG. 7 shows a wearable processing device 2, according to one embodiment.
Figure 8:
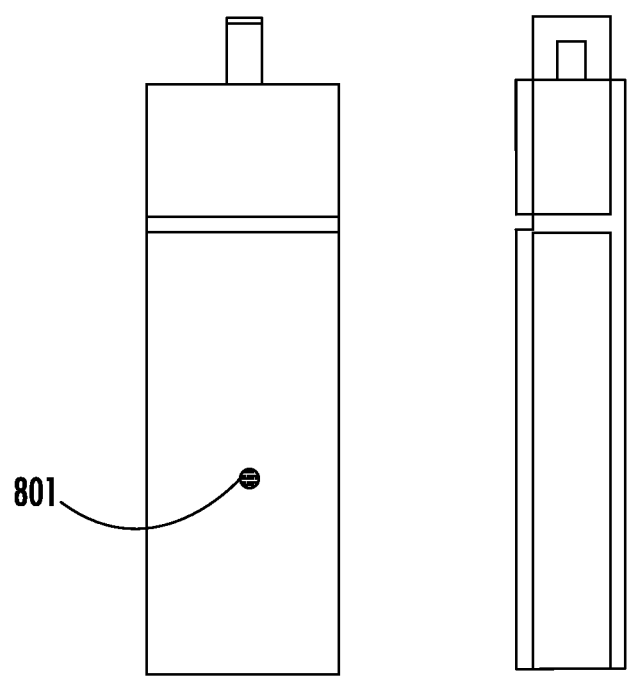
FIG. 8 shows a processing device 3, according to one embodiment.
Figure 10:
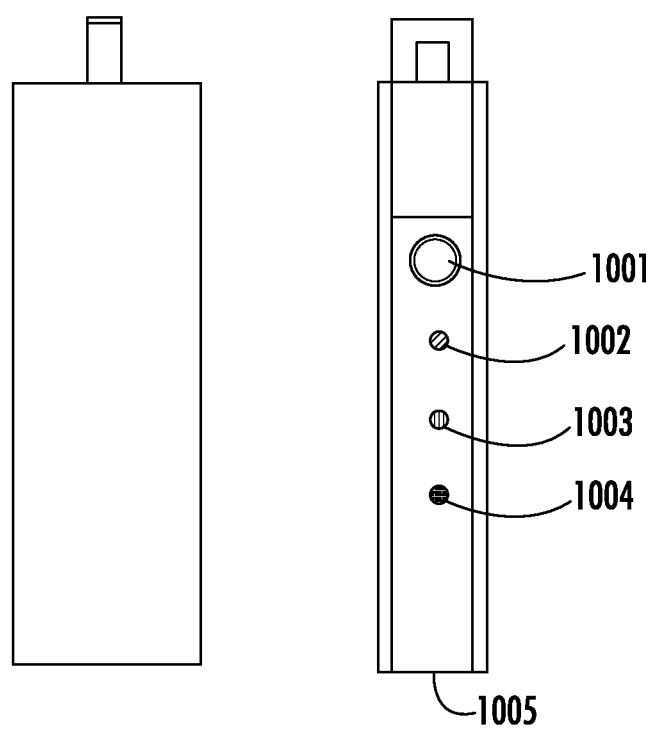
FIG. 10 shows a processing device 4, according to one embodiment. Green, red, and yellow lights are provided to reveal the results of the food allergen test. Green light shows the absence of the food allergen. Red light shows the presence of the food allergen Flashing yellow light shows that reading is in progress, and a stable yellow light represent an inconclusive reading.

The sensor chips may be part of the disposable portion of the test and may connect to the re-usable reader or a processing device (the "Amulet"). The Amulet may contain the necessary electronics (multimeter/potentiostat/microprocessor/physical memory) to analyze the chips. FIGS. 1-3 shows illustrative embodiments of the printed circuit boards of the Amulet. Referring to FIG. 1, the Amulet may have a housing consisting of a top part 101, a short end side part 102, and a bottom part 104, that contains within a printed circuit board configured to connect to a MicroSD connector of a removable part of the food allergen detection device 105 described above. The assembled Amulet may have a push button 106 configured to initiate reading of electrical resistance in the food allergen detection device. The Amulet may further have a surface mounted green led light 107 that lights up if the food allergen is absent, a surface mounted red led light 108 that lights up if the food allergen is detected, and a surface mounted yellow light 109 that indicates reading in process by flashing and inconclusive result if the yellow light is stable. FIGS. 2 and 3 show illustrative embodiments of the circuit board for the processing device. In some embodiments, as illustrated in FIG. 4 or FIG. 6, the green light 401 or 601, the red light 402 or 602, and the yellow light 403 or 603, may be on the front side 404 or 604 of the processing device. In some embodiments, as illustrated in FIG. 10, the green light 1002, the red light 1003, and the yellow light 1003, may be on the side 1005 of the processing device. In some embodiments, the processing device may have a push button 1001 to initiate the reading of the food allergen detection device. In some embodiments, the processing device may only have one light mounted on the surface to read the result of the food allergen testing. FIG. 5 shows an embodiment of the device having one light 503 mounted on the surface. FIG. 7 shows another embodiment of a device having one light 703 mounted on the surface. FIG. 8 shows another embodiment of a device having one light 801 mounted on the surface.

A typical disposable component may contain multiple sensor chips, including one or more with polymers imprinted to recognize one or more tracer molecules. The device may contain one or more control chips, either non-imprinted or imprinted against a chosen interferent molecule.

The relative measurements of each chip are used to determine whether the target ingredient is present. Readings for each chip may be taken once, multiple times, or continuously. In some embodiments, the device may further comprise a processing device, wherein the processing device is configured to communicatively couple to the sensor chip, wherein the processing device is configured to determine a resistance difference between a resistance of the molecularly imprinted polymer layer and a resistance of the non-imprinted polymer layer. In further embodiments, the processing device determines the presence of the first food allergen when the resistance of the resistance of the molecularly imprinted polymer layer is greater than the resistance of the non-imprinted polymer layer. In another embodiment, the processing device determines the presence of the first food allergen when the resistance of the resistance of the molecularly imprinted polymer layer is less than the resistance of the non-imprinted polymer layer.

In another aspect, the device comprises a processing device. FIGS. 1-11 show illustrative embodiments of the processing device. In some embodiments, the processing device is configured to communicatively couple to the sensor. In some embodiments, the processing device comprises circuitry configured to determine presence of the food allergen. In another embodiment, to determine presence of the food allergen the processing device is configured to compare a resistance of the MIP to the resistance of the NIP. In further embodiments, the processing device is configured to determine a resistance difference between a resistance of the MIP and a resistance of the NIP; compare the resistance difference to a threshold difference. In further embodiments, the processing device is configured to determine that the food allergen is present when the resistance difference is greater than the threshold difference. In further embodiments, the processing device determines that the food allergen is present when the resistance of the MIP is greater than the resistance of the NIP. In yet further embodiments, the processing device determines that the food allergen is present when the resistance of the MIP is less than the resistance of the NIP.

Figure 9:
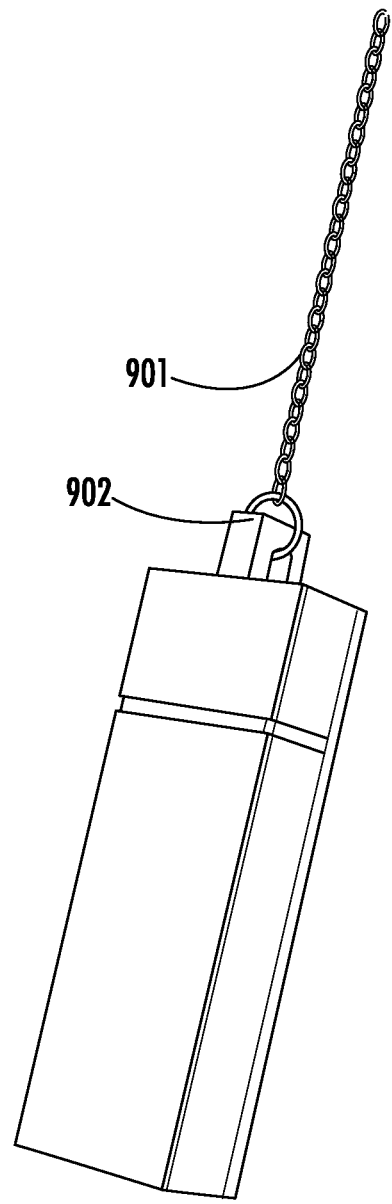
FIG. 9 shows a wearable processing device 3, according to one embodiment.
Figure 11:
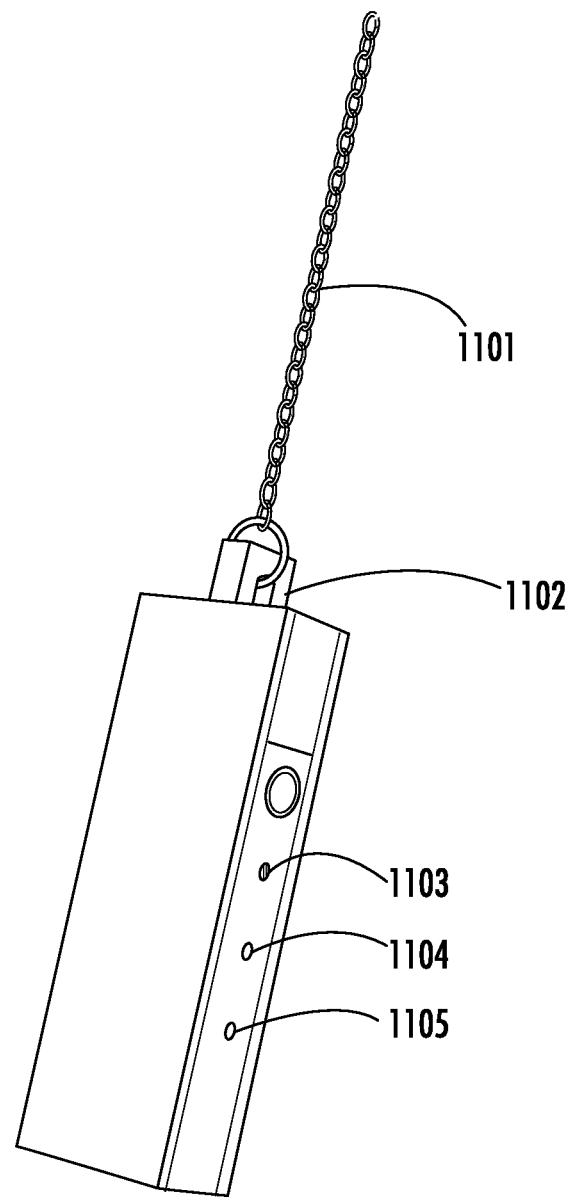
FIG. 11 shows a wearable processing device 4, according to one embodiment.

In another embodiment, the processing device communicatively couples to the sensor via a plurality of contacts of the sensor and via a plurality of contacts of the processing device. In further embodiments, the processing device is a wearable. FIGS. 5, 7, 9, and 11 show illustrative embodiments of a wearable processing device. Referring to FIG. 5, a chain 501 is connected to a hook 502 that is part of the processing device, so that the device can be placed around the neck of the subject wearing the device. Referring to FIG. 7, a chain 701 is connected to a hook 702 that is part of the processing device, so that the device can be placed around the neck of the subject wearing the device. Referring to FIG. 9, a chain 901 is connected to a hook 902 that is part of the processing device, so that the device can be placed around the neck of the subject wearing the device. Referring to FIG. 11, a chain 1101 is connected to a hook 1102 that is part of the processing device, so that the device can be placed around the neck of the subject wearing the device. In another embodiment, the processing device communicatively couples to the sensor via a wireless signal. In further embodiments, the wireless signal comprises a radio and/or infrared frequency signal. In yet further embodiments, the processing device is a computer, telephone, watch, and/or mobile device.

Methods of Use

The present technology provides a convenient method to detect allergens in food. In some embodiment, the present disclosure provides a method for detecting a food allergen using the food allergen detection device described herein, comprising exposing the sensor to the food.

The method of detecting a food allergen, further comprising: a) exposing the substrate to the food; and b) inserting the substrate into the chamber. Upon inserting the substrate into the chamber, the substrate punctures a capsule filled with solvent. Hence, in some embodiments the method comprising the steps of, the inserting the substrate into the chamber punctures the capsule and releases the liquid into the reservoir. In some embodiments, the method further comprises the step of agitating the device. In yet further embodiments, the agitating comprises shaking.

After the food sample has been inserted into the device, and the food has been mixed with a solvent, the user moves the sensor to a second position such that a portion of the printed circuit board is outside the body of the device. Accordingly, in some embodiments, the method further comprises moving the sensor to the second position such that a portion of the printed circuit board is outside of the body of the device. Then, the user inserts the exposed portion of the circuit board into the processing device. FIGS. 4-11 shows illustrative embodiments of processing devices. Hence, in some embodiments, the method further comprises inserting the portion of the printed circuit board outside of the body of the device into the processing device.

Finally, the user can read the result of the processing device. Accordingly, in some embodiments, the method further comprises viewing the processing device results. FIGS. 4, 6, and 10 show processing devices having red, green, and yellow lights to reveal the presence food allergen. In some embodiments, when the food allergen is present the processing device displays a red light. In other embodiments, when the food allergen is absent the processing device displays a green light.

In another aspect, the present disclosure provides a method of manufacturing the device described herein.

The present invention, thus generally described, will be understood more readily by reference to the following examples, which are provided by way of illustration and are not intended to be limiting of the present invention.

EXAMPLES

The examples herein are provided to illustrate advantages of the present technology and to further assist a person of ordinary skill in the art with preparing or using the compositions of the present technology. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

Example 1: Manufacturing a Sensor Chip

Combine polymer, template molecule, conductive material, and solvent in a vial and stir at room temperature for 6+ hours. This allows for solution-phase interaction of polymer and template molecule, where the polymer chains may fold around the template molecules and establish hydrogen bonding networks (among other Van der Waals interactions).

1) A typical mixture:
5 ml dimethyl formamide (solvent)
500 mg poly(4-vinylphenol) (polymer)
200 mg genistein (template molecule)
50 mg carbon nanotubes (conductive material)
2) Coat an interdigitated circuit board with the above mixture.

The PCBs are typically 1 cm square FR4 boards with two electrodes consisting of interlacing copper 'fingers'. The spacing between the copper digits is typically 150 um.

A PCB is placed onto a spin coater, ~75 ul of solution is pipetted onto the surface, and the chip is spun at 3000 RPM for 30 seconds, evaporating most of the solvent and depositing a thin polymer film.

The polymer-coated PCB is placed in an oven at 70 degrees Celsius for at least 2 hours to evaporate any remaining solvent.

Baseline measurements are taken for the film after it is baked (resistance and IR spectroscopy). At this stage the cavities in the polymer are still occupied by the starting template molecule.

3) Template molecule is washed from film.

Film is placed in 10 ml of basic aqueous solution for 30 minutes to remove genistein.

Second identical wash in fresh 10 ml wash solution.

Film is oven-dried and further reference IR and resistance measurements are taken. At this point the cavities in the polymer should all be empty.

4) The film is ready for rebinding trials. The film is placed into challenge solutions of interest for variable amounts of time.

Rebinding of template molecule should be visible in characteristic IR absorption peaks and in increased resistance measurements.

Parallel to steps 1-4, non-imprinted polymer (NIP) control chips are produced and tested. These are analogous to the molecularly imprinted polymer (MIP) sensor chips, but the starting polymer mixture does not include any template molecule. The NIP chips should exhibit similar non-specific interactions with the solutions and control for most factors other than the specific binding of the template molecule to the cavities in the MIP film (wetness, salinity, non-specific binding, etc.)

For the resistance measurements, electricity is conducted between the copper electrodes by the carbon nanotubes embedded in the non-conductive polymer films. The nanotubes are electrically doped by adjacent molecules. When the cavities are occupied by template molecules, this changes the conductivity of adjacent nanotubes (and thus the film).

Example 2: Synthesis of Molecularly Imprinted Cross-Linked Polymer

The imprinted polymer is synthesized as nanoparticles. Methyl methacrylate (MMA) monomer, ethylene glycol dimethacrylate (EGDMA) cross-linker (molar ratio of 1:2 to 5:1 of cross-linker to monomer), and azobisisobutyronitrile (AIBN) radical initiator are dissolved with genistein (the template molecule) in ethanol (template molar ratio of 1:2 to 1:20 to monomer). The mixture is purged with nitrogen and then stirred and incubated at 65° C. to initiate precipitation polymerization. After 2 hours of polymerization the resulting milky suspension is cooled and filtered. The solid nanoparticles (diameter approximately 50 nm to 1000 nm, or from 200 nm to 600 nm) are placed in a Soxhlet extractor and washed with refluxing ethanol for 2 hours to remove the template molecule.

Example 3: Synthesis of Molecularly Imprinted Non-Cross-Linked Polymer

Soluble polymer such as poly(4-vinylphenol) dissolved in solvent such as ethanol or dimethylformamide (DMF). Multi-walled carbon nanotubes are added and the mixture is sonicated to create a stable suspension. Template molecule (genistein) is added and the mixture is stirred overnight. The mixture is spin-casted onto interdigitated sensor chips. The template molecule is removed by washing with an orthogonal solvent. Re-binding of the template/ tracer molecule is measured spectroscopically, or by resistance readings.

Example 4: MIP Nanoparticles Incorporated on Electrochemical Chip for CV Experiment The MWCNT make the film conductive, so these sensor chips can be used for 2-point resistance measurements. The type of CNT, ratio of CNT, and film thickness can be used to control the starting resistance values for the films. SEM images show that the CNTs wrap around the nanoparticles. Binding of the tracer/template molecule to the surface of the imprinted polymer is understood to modulate electron densities and swell the nanoparticles, changing the film resistance. The resulting sensor chips may be tuned to have resistances in the range of about 10 ohms to about 1,000,000 ohms. Sensor chips with higher conductivities are appropriate for submerged resistance measurements. If the chip is substantially more conductive than the shorting pathway through the sample solution (often about 100,000 ohms), the shorting pathway becomes negligible in the overall measured resistance. When using sensor chips with low starting resistances, changes in the measured resistance are primarily caused by the swelling and dopant effects of the sample.

In a typical experiment, two sensor chips, one fabricated with MIP nanoparticles in the film and one fabricated with NIP nanoparticles in the film are submerged in the same test solution. The relative change in resistance for each film over time is measured. Significant differences between the two films indicates that the target tracer molecule is present in the test solution. Anchor polymer (polyvinylphenol) is mixed with ethanol, multi-walled carbon nanotubes (MWCNT) are added, and the mixture is sonicated with a tip sonicator to create a stable dispersion. Nanoparticles (MIP or NIP) are added and the mixture is stirred and sonicated briefly in a sonication bath. FIGS. 20-21 shows the resulting MIP MWCNT wrapped nanoparticles. A few μl (for example, 1 μl to 10 μl) of the solution is drop-cast onto the electrochemical chip, and the chip is baked in a convection oven at 70° C. to fully evaporate the ethanol solvent.

The electrochemical chips have a carbon working electrode, a carbon counter electrode and a silver/ silver chloride reference electrode.

A standard electrochemical experiment is run by submerging the chip in an electrolyte solution such as $KCl/K_3Fe(CN)_6/K_4Fe(CN)_6$. A typical cyclic voltammetry (CV) experiment from −0.5 to +1 volts at a scan rate of 10-100 mV/s. The sensor chip is then placed in contact with a sample for a period of incubation (for example, 1 to 30 minutes). The incubation solution may contain any aqueous buffer or organic solvent which does not degrade the sensing film but does dissolve the target tracer molecule. After incubation with sample, the sensor chip is once again placed in the electrolyte solution and a second CV is taken. Comparison of before and after CVs is used to determine whether tracer molecule has been bound. Typical behavior is for bound template molecule to reduce the maximum oxidation current.

One or more control chips containing NIP nanoparticles on the working electrode, or MIP particles imprinted for a non-target molecule may be employed in the test. The electrochemistry and rebinding experiments described above are performed in parallel for these control chips, and the difference between control sensor response and targeted MIP sensor response is used to determine whether the target molecule is present in the sample.

Exemplary Embodiments

Para. A. In one aspect, the present technology provides a device including a sensor comprising a printed circuit board comprising a chip comprising a molecularly imprinted polymer (MIP) and a non-imprinted polymer (NIP); a reservoir comprising a liquid; and a chamber for mixing the liquid with a food.

Para. B. The device of Para. A, wherein a body surrounds at least partially the sensor, the reservoir, and the chamber.

Para. C. The device of Para. B, wherein the body is configured to receive a substrate with the food on a surface of the substrate.

Para. D. The device of any one of Para. A-Para.C, wherein the reservoir comprises a capsule that encapsulates the liquid.

Para. E. The device of any one of Para. A-Para. D, wherein the liquid comprises a solvent.

Para. F. The device of Para. E, wherein the solvent comprises water.

Para. G. The device of any one of Para. A-Para. F, wherein the liquid comprises a buffer.

Para. H. The device of any one of Para. A-Para. G, wherein the device further comprises a locking mechanism for locking the substrate into the chamber.

Para. I. The device of Para. H, wherein the locking mechanism comprises a ramp.

Para. J. The device of Para. I, wherein the ramp is adjacent to the reservoir.

Para. K. The device of Para. J, wherein compression of the ramp punctures the capsule releasing the liquid into the reservoir.

Para. L. The device of any one of Para. A-Para. K, wherein the device further comprises a recess configured to house the sensor.

Para. M. The device of Para. L, wherein the recess has a first portion for housing the sensor in a first position and a second portion for housing the sensor in a second position, the first and the second portions being linked such that the sensor is moveable from the first position to the second position in the recess.

Para. N. The device of Para. M, wherein when in the first position the chip is in contact with the reservoir.

Para. O. The device of Para. M or Para. N, wherein when in the second position the chip is not in contact with the reservoir.

Para. P. The device of any one of paragraphs Para. M-Para. O, wherein when in the second position a portion of the printed circuit board is outside of the body.

Para. Q. The device of any one of Para. M-Para. P, further comprising an access port communicating with the recess for manual movement of the sensor between the first and second positions.

Para. R. The device of any one of Para. A- Para. Q, wherein the NIP comprises a film.

Para. S. The device of any one of Para. A- Para. R, wherein the MIP comprises a film.

Para. T. The device of any one of Para. A-Para. S, wherein the MIP comprises receptor sites for a food allergen.

Para. U. The device of Para. T, wherein the food allergen comprises a molecule with a molecular weight less than about 5000 g/mol.

Para. V. The device of Para. T or Para. U, wherein the food allergen comprises a peanut allergen, tree nut allergen, milk allergen, egg allergen, wheat allergen, soy allergen, meat allergen, fish allergen, shellfish allergen, coconut allergen, or a combination of two or more thereof.

Para. W. The device of any one of Para. T-Para. V, wherein the food allergen comprises a nut allergen listed in Table 1.

Para. X. The device of Para. V, wherein the tree nut allergen comprises almond, almond paste, or a combination thereof.

Para. Y. The device of any one of Para. T-Para. X, wherein the food allergen comprises a soy allergen.

Para. Z. The device of any one of Para. T-Para. Y, wherein the food allergen comprises a flavonoid, amygdalin, or a combination thereof.

Para. AA. The device of Para. Z, wherein the flavonoid comprises an isoflavonoid, neoflavonoid, or derivatives thereof Para. AB. The device of Para. AA, wherein the isoflavonoid or derivative thereof comprises isoflavones, isoflavonones, isoflavans, pterocarpans, rotenoids, or combinations of two or more thereof.

Para. AC. The device of any one of Para. T-Para. AB, further comprising the substrate.

Para. AD. The device of Para. AC, wherein the substrate comprises glass, plastic, paper, quartz, alumina, mica, silicon, a III-IV semiconductor compound, or combinations of two or more thereof.

Para. AE. The device of paragraphs Para. AC or Para. AD, wherein the substrate has an elongated shape.

Para. AF. The device of any one of Para. AC-Para. AE, wherein the substrate has a top and a bottom.

Para. AG. The device of Para. AF, wherein the bottom has a tapered end and/or the top has a portion for holding the substrate.

Para. AH. The device of any one of Para. AC-Para. AG, wherein the substrate comprises one or more holes and/or cervices.

Para. AI. The device of any one of Para. AC-Para. AH, wherein the substrate is disposable.

Para. AJ. The device of any one of Para. AC-Para. AI, wherein the substrate is recyclable.

Para. AK. The device of any one of Para. AC-Para. AJ, wherein the substrate further comprises a wireless transceiver.

Para. AL. The device of any one of Para A-Para. AK, wherein the device further comprises a processing device.

Para. AM. The device of Para. AL, wherein the processing device is configured to communicatively couple to the sensor.

Para. AN. The device of Para. AL or Para. AM, wherein the processing device comprises circuitry configured to determine presence of the food allergen.

Para. AO. The device of Para. AN, wherein to determine presence of the food allergen the processing device is configured to compare a resistance of the MIP to the resistance of the NIP.

Para. AP. The device of any one of Para. AL-Para. AO, wherein the processing device is configured to determine a resistance difference between a resistance of the MIP and a resistance of the NIP; compare the resistance difference to a threshold difference.

Para. AQ. The device of any one of Para. AL-Para. AP, wherein the processing device is configured to determine that the food allergen is present when the resistance difference is greater than the threshold difference.

Para. AR. The device of any one of Para. AL-Para. AQ, wherein the processing device determines that the food allergen is present when the resistance of the MIP is greater than the resistance of the NIP.

Para. AS. The device of any one of Para. AL-Para. AR, wherein the processing device determines that the food allergen is present when the resistance of the MIP is less than the resistance of the NIP.

Para. AT. The device of any one of Para. AL-Para. AS, wherein the processing device communicatively couples to the sensor via a plurality of contacts of the sensor and via a plurality of contacts of the processing device.

Para. AU. The device of any one of Para. AL-Para. AT, wherein the processing device is a wearable.

Para. AV. The device of any one of Para. AL-Para. AU, wherein the processing device communicatively couples to the sensor via a wireless signal.

Para. AW. The device of Para. AV, wherein the wireless signal comprises a radio and/or infrared frequency signal.

Para. AX. The device of Para. AV or Para. AW, wherein the processing device is a computer, telephone, watch, and/or mobile device.

Para. AY. In another aspect, the present disclosure provides a method for detecting a food allergen using the device of any one of Para. A to Para. AX, comprising exposing the sensor to the food.

Para. AZ. The method of Para. AY, further comprising:
a) exposing the substrate to the food; and
b) inserting the substrate into the chamber.

Para. BA. The method of Para. AZ, wherein the inserting the substrate into the chamber punctures the capsule and releases the liquid into the reservoir.

Para. BB. The method of Para. AZ or Para. BA, further comprising agitating the device.

Para. BC. The method of Para. BB, wherein the agitating comprises shaking.

Para. BD. The method of any one of Para. AY-Para. BC, further comprising moving the sensor to the second position such that a portion of the printed circuit board is outside of the body of the device.

Para. BE. The method of Para. BD, further comprising inserting the portion of the printed circuit board outside of the body of the device into the processing device.

Para. BF. The method of any one of Para. AY-Para. BE, further comprising viewing the processing device results.

Para. BG. The method of Para. BF, wherein when the food allergen is present the processing device displays a red light.

Para. BH. The method of Para. BF or Para. BG, wherein when the food allergen is absent the processing device displays a green light.

Para. BI. In another aspect, the present disclosure provides a method of manufacturing the device of any one of Para. A to Para. BH.

Equivalents

While certain embodiments have been illustrated and described, a person with ordinary skill in the art, after reading the foregoing specification, can effect changes, substitutions of equivalents and other types of alterations to the compositions of the present technology as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, or compositions, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:

1. A device comprising: a food allergen detection platform comprising:
    a substrate;
    a molecularly imprinted polymer layer in contact with the substrate, the molecularly imprinted polymer layer comprising receptor sites imprinted in a first surface of a polymer, the receptor sites configured to accept a trace molecule of a food allergen;
    a non-imprinted polymer layer in contact with the substrate, wherein the non-imprinted polymer layer comprises the polymer which is not imprinted with receptor sites;
    a sensor chip comprising the molecularly imprinted polymer and the non-imprinted polymer, which is configured to detect the presence of the trace molecule upon binding to one or more of the receptor sites on the molecularly imprinted polymer; and
    a recess configured to house the sensor chip wherein the recess has a first portion for housing the sensor chip in a first position and a second portion for housing the sensor chip in a second position, the first and the second portions being linked such that the sensor chip is moveable from the first position to the second position in the recess.

2. The device of claim 1, wherein the device further comprises a processing device, wherein the processing device is configured to communicatively couple to the sensor chip, wherein the processing device is configured to determine a resistance difference between a resistance of the molecularly imprinted polymer layer and a resistance of the non-imprinted polymer layer.

3. The device of claim 2, wherein the processing device determines the presence of the food allergen when the resistance of the molecularly imprinted polymer layer is greater than the resistance of the non-imprinted polymer layer.

4. The device of claim 2, wherein the processing device determines the presence of the food allergen when the resistance of the molecularly imprinted polymer layer is less than the resistance of the non-imprinted polymer layer.

5. The device of claim 1, wherein the substrate comprises a glass, a plastic, a paper, a quartz, alumina, mica, silicon, a Group III-IV semiconductor compound, or a combination of any two or more thereof.

6. The device of claim 1, wherein the polymer comprises a poly(4-vinylphenol), a poly(urethane), a poly(methylmethacrylate), a poly(methacrylic acid), poly(hydroxyethylmethacrylate), poly(vinylpyrrolidone), a co-polymer of any two or more there, or a polymer blend of any two or more thereof.

7. The device of claim 1, wherein the polymer is a cross-linked polymer.

8. The device of claim 1, wherein the polymer is a non-cross-linked polymer.

9. The device of claim 1, further comprising a reservoir, wherein the reservoir comprises a capsule that encapsulates a solvent; and a chamber for mixing the solvent with food.

10. The device of claim 9, wherein the solvent is water, a buffer, a saline solution, an organic solvent, or any combination thereof.

11. The device of claim 10, wherein the device further comprises a locking mechanism for locking the substrate into the chamber.

12. The device of claim 11, wherein the locking mechanism comprises a ramp adjacent to the reservoir.

13. The device of claim 12, wherein compression of the ramp punctures the capsule releasing the liquid into the reservoir.

14. The device of claim 1, wherein when in the first position the sensor chip is in contact with a reservoir, and wherein when in the second position the sensor chip is not in contact with the reservoir.

15. The device of claim 1, wherein the trace molecule of the food allergen is an organic molecule.

16. The device of claim 15, wherein the organic molecule has a molecular weight of less than about 900 Daltons.

17. The device of claim 15, wherein the organic molecule is selected from lactose, galactose, amygdalin, juglone, biochanin A, resveratrol daidzein, daidzin, and genistin.

18. The device of claim 1, wherein the molecule of the food allergen is a polypeptide, epitope, aptamer, or protein.

* * * * *